(12) United States Patent
Nakatsuru et al.

(10) Patent No.: US 10,046,304 B2
(45) Date of Patent: Aug. 14, 2018

(54) WATER ABSORBING AGENT AND METHOD FOR PRODUCING THE SAME

(71) Applicant: NIPPON SHOKUBAI CO., LTD., Osaka (JP)

(72) Inventors: Reiko Nakatsuru, Himeji (JP); Nobuya Tanaka, Himeji (JP); Yoshiro Mitsukami, Himeji (JP)

(73) Assignee: NIPPON SHOKUBAI CO., LTD., Osaka (JP)

(*) Notice: Subject to any disclaimer, the term of this patent is extended or adjusted under 35 U.S.C. 154(b) by 67 days.

(21) Appl. No.: 14/433,282

(22) PCT Filed: Oct. 3, 2013

(86) PCT No.: PCT/JP2013/076938
§ 371 (c)(1),
(2) Date: Apr. 2, 2015

(87) PCT Pub. No.: WO2014/054731
PCT Pub. Date: Apr. 10, 2014

(65) Prior Publication Data
US 2015/0273433 A1 Oct. 1, 2015

(30) Foreign Application Priority Data
Oct. 3, 2012 (JP) .................. 2012-221748

(51) Int. Cl.
| | | |
|---|---|---|
| B01J 20/26 | (2006.01) | |
| C08L 33/08 | (2006.01) | |
| A61F 13/53 | (2006.01) | |
| C08J 3/24 | (2006.01) | |
| B01J 20/30 | (2006.01) | |
| C08J 3/075 | (2006.01) | |

(52) U.S. Cl.
CPC ............ B01J 20/267 (2013.01); A61F 13/53 (2013.01); B01J 20/3007 (2013.01); C08J 3/075 (2013.01); C08J 3/245 (2013.01); C08L 33/08 (2013.01); *A61F 2013/530481* (2013.01); *A61F 2013/530708* (2013.01); *A61F 2013/530788* (2013.01); *B01J 2220/68* (2013.01); *C08J 2333/02* (2013.01)

(58) Field of Classification Search
None
See application file for complete search history.

(56) References Cited

U.S. PATENT DOCUMENTS

| | | | |
|---|---|---|---|
| 4,703,067 A | 10/1987 | Mikita et al. | |
| 5,002,986 A | 3/1991 | Fujiura et al. | |
| 5,124,188 A | 6/1992 | Roe et al. | |
| 5,154,713 A | 10/1992 | Lind | |
| 5,314,420 A | 5/1994 | Smith et al. | |
| 5,399,591 A | 3/1995 | Smith et al. | |
| 5,451,613 A | 9/1995 | Smith et al. | |
| 5,462,972 A | 10/1995 | Smith et al. | |
| 5,624,967 A | 4/1997 | Hitomi et al. | |
| 5,633,316 A * | 5/1997 | Gartner ................ | A61L 15/48 525/329.1 |
| 5,712,316 A | 1/1998 | Dahmen et al. | |
| 5,856,370 A | 1/1999 | Chmelir | |
| 5,985,944 A | 11/1999 | Ishizaki et al. | |
| 6,107,358 A | 8/2000 | Harada et al. | |
| 6,136,873 A | 10/2000 | Hahnle et al. | |
| 6,562,879 B1 * | 5/2003 | Hatsuda ................ | C08J 3/12 241/24.28 |
| 6,710,141 B1 | 3/2004 | Heide et al. | |
| 6,750,262 B1 | 6/2004 | Hahnle et al. | |
| 6,939,914 B2 | 9/2005 | Qin et al. | |
| 7,091,253 B2 | 8/2006 | Dairoku et al. | |
| 7,265,190 B2 | 9/2007 | Dairoku et al. | |
| 8,017,549 B2 | 9/2011 | Herfert et al. | |
| 2005/0176834 A1 | 8/2005 | Hintz et al. | |

(Continued)

FOREIGN PATENT DOCUMENTS

| | | |
|---|---|---|
| EP | 0450922 | 10/1991 |
| EP | 0595803 | 5/1994 |

(Continued)

OTHER PUBLICATIONS

International Preliminary Report on Patentability for PCT/JP2013/076938, dated Apr. 16, 2015.

(Continued)

*Primary Examiner* — Joseph D Anthony
(74) *Attorney, Agent, or Firm* — Dickinson Wright PLLC

(57) ABSTRACT

The present invention provides (i) a water absorbing agent which is excellent in a water absorbing physical properties, in particular water absorbing speed and has a great bulk specific gravity and (ii) a method for producing the water absorbing agent. The method for producing the water absorbing agent includes a surfactant adding step of adding a surfactant whose HLB is 10 or less. The surfactant adding step is the step of adding a dispersion liquid, which contains the surfactant equivalent to 30 parts by weight to 150 parts by weight, relative to 1000000 parts by weight of a water absorbent resin solid content, and the surfactant adding step is carried out after a drying step. Further, in a case where a water-soluble polyvalent metal salt adding step is carried out after the drying step, the surfactant adding step is carried out after the water-soluble polyvalent metal salt adding step.

4 Claims, No Drawings

(56) References Cited

U.S. PATENT DOCUMENTS

| | | | |
|---|---|---|---|
| 2005/0209352 A1* | 9/2005 | Dairoku | A61L 15/60 521/50 |
| 2007/0015860 A1 | 1/2007 | Frank | |
| 2007/0207924 A1* | 9/2007 | Ikeuchi | C08J 3/245 502/402 |
| 2007/0225422 A1 | 9/2007 | Sakamoto et al. | |
| 2008/0269372 A1 | 10/2008 | Dairoku et al. | |
| 2010/0093949 A1* | 4/2010 | Herfert | A61F 13/53 525/451 |
| 2010/0119312 A1* | 5/2010 | Nagashima | A61L 15/60 406/46 |
| 2010/0234531 A1 | 9/2010 | Frank | |
| 2010/0268181 A1 | 10/2010 | Ziemer et al. | |
| 2011/0313113 A1 | 12/2011 | Sakamoto et al. | |
| 2012/0184670 A1 | 7/2012 | Kobayashi et al. | |
| 2012/0258851 A1 | 10/2012 | Nakatsuru et al. | |
| 2013/0026412 A1 | 1/2013 | Machida et al. | |
| 2013/0101851 A1 | 4/2013 | Takaai et al. | |
| 2014/0296465 A1 | 10/2014 | Sakamoto et al. | |
| 2015/0273433 A1* | 10/2015 | Nakatsuru | A61F 13/53 252/194 |

FOREIGN PATENT DOCUMENTS

| | | |
|---|---|---|
| EP | 1521601 | 4/2005 |
| EP | 1957188 | 8/2008 |
| JP | 63-105064 | 5/1988 |
| JP | 1-318021 | 12/1989 |
| JP | 5-156034 | 6/1993 |
| JP | 2000-302876 | 10/2000 |
| JP | 2005-162834 | 6/2005 |
| JP | 2007-529295 | 10/2007 |
| JP | 2010-510045 | 4/2010 |
| WO | 91/15368 | 10/1991 |
| WO | 92/18171 | 10/1992 |
| WO | 94/022502 | 10/1994 |
| WO | 95/02002 | 1/1995 |
| WO | 97/017397 | 5/1997 |
| WO | 00/052087 | 9/2000 |
| WO | 2005/012406 | 2/2005 |
| WO | 2005/063313 | 7/2005 |
| WO | 2005/075070 | 8/2005 |
| WO | 2008/120742 | 10/2008 |
| WO | 2009/062902 | 5/2009 |
| WO | 2011/040472 | 4/2011 |
| WO | 2011/040530 | 4/2011 |
| WO | 2011/078298 | 6/2011 |
| WO | 2012/133734 | 10/2012 |

OTHER PUBLICATIONS

International Search Report for PCT/JP2013/076938, dated Dec. 17, 2013, and English translation thereof.

* cited by examiner

WATER ABSORBING AGENT AND METHOD FOR PRODUCING THE SAME

TECHNICAL FIELD

The present invention relates to a water absorbing agent and a method for producing the water absorbing agent. More specifically, the present invention relates to (i) a particulate water absorbing agent whose main component is a polyacrylic acid (salt)-based water absorbent resin and which has a particular water absorption performance and (ii) a method for producing the particulate water absorbing agent.

BACKGROUND ART

The water absorbent resin (SAP/Super Absorbent Polymer) is a water-swelling and water-insoluble polymer gelatinizer and is used mainly for disposable purpose, i.e., for absorbing articles such as a disposable diaper and a sanitary napkin and for an agriculture/horticulture water retention agent, an industrial waterproofing material, and the like. Various kinds of monomers and hydrophilic polymers have been proposed as a raw material for such a water absorbent resin. In particular, a polyacrylic acid (salt)-based water absorbent resin in which acrylic acid and/or salt thereof is used as a monomer(s) is industrially most widely used because of its high water absorption performance.

Such a water absorbent resin is produced through a polymerization step, a drying step, an undried substance removing step (if needed), a pulverizing step, a classification step, a surface crosslinking step, and the like (see Patent Literatures 1 through 5).

Moreover, in accordance with advancement of a disposable diaper which is the main purpose of use of the absorbent resin, the water absorbent resin is demanded to have various functions. Specifically, not only a high water absorption capacity, various physical properties such as a gel strength, a water soluble component, a water absorbing speed, a water absorption capacity under load, a liquid permeability, a particle size distribution, a urine resistance, an antibacterial property, an impact resistance (damage resistance), a powder fluidity, a deodorizing property, a fluidity, a filling ability, a coloration resistance (whiteness), and a dust suppression property are requested of the water absorbent resin. Under the circumstances, various proposals concerning surface crosslinking techniques, additives, change in production process, and the like have been made in Patent Literatures below, in addition to the above cited Patent Literatures.

In recent years, among the above described physical properties, the water absorbing speed is becoming a more important factor in accordance with increase in used amount (e.g., 50 wt % or more) of a water absorbent resin in a disposable diaper.

As a method for improving the water absorbing speed, a technique is known by which the water absorbing speed is improved by increasing a specific surface area. Specifically, various techniques have been proposed as follows: that is, a technique to minutely control a particle diameter (Patent Literature 6), a technique to prepare fine particles having a large surface area (Patent Literatures 7 through 9), a technique to causing a hydrogel to become porous by freeze-drying (Patent Literature 10), a technique to carry out surface crosslinking simultaneously with preparing particles (Patent Literatures 11 through 13), a technique of foaming polymerization (Patent Literatures 14 through 32), a technique of foaming and crosslinking after polymerization (Patent Literature 33), and the like.

According to the techniques of Patent Literatures 6 through 33 and the like, the water absorbing speed is increased by, for example, increasing the specific surface area of the water absorbent resin. However, the techniques have a problem such as decrease in bulk specific gravity. The decrease in bulk specific gravity causes problems that, when a container is filled with a water absorbent resin for transportation or the like, (i) a predetermined weight of the water absorbent resin cannot be put in the container or (ii) vibrational operation is required in filling and therefore a water absorbent resin is damaged, and the like. In general, the water absorbing speed and the specific surface area have a positive correlation, and the bulk specific gravity and the specific surface area have a negative correlation. It is therefore difficult to maintain the bulk specific gravity while increasing the water absorbing speed that greatly depends on the specific surface area.

A method for increasing the bulk specific gravity has been proposed before the water absorbing speed is focused on. For example, techniques such as follows have been proposed, i.e., a technique in which a bulk specific gravity and an absorption capacity under load are increased by carrying out surface crosslinking after water absorbent resin particles are polished (Patent Literature 34), and a technique in which a fluidity and a bulk specific gravity are increased by adding a powder lubricant or surfactant (Patent Literature 35). However, in Patent Literature 34, the number of processes for producing a water absorbent resin is increased by the polishing of a surface of the water absorbent resin, and it is also necessary to deal with fine powder generated by the polishing. Therefore, the technique of Patent Literature 34 has a problem that a cost and workload for the production is increased. Moreover, according to a water absorbent resin in Patent Literature 35, the added lubricant and surfactant are eluted into an absorbed liquid and therefore a surface tension of the absorbed liquid is decreased, and this causes increase in returned liquid amount in absorbent articles.

Meanwhile, as a method for improving a fluidity and a transport property which are expected to bring about an effect similar to improvement in bulk specific gravity, techniques such as follows have been proposed, i.e., a technique to add stearic acid and inorganic powder (Patent Literature 36), a technique to add an aggregation controlling agent such as alcohol or polyglycol (Patent Literature 37), and a technique to add metallic soap (Patent Literatures 38 and 39). However, although improvement in bulk specific gravity can be expected by the use of these techniques, not all the techniques necessarily improve the bulk specific gravity. Moreover, according to Patent Literature 37, a water absorbent resin is characterized by being fed well by vibrational filling. However, it may be preferable to fill the container with the water absorbent resin without carrying out vibrational filling, that is, the bulk specific gravity is preferably lower because the number of processes can be reduced and the water absorbent resin would be less damaged. Further, Patent Literature 40 which is an unpublished earlier application also discloses to add a surfactant after surface crosslinking. However, it has been found that, in some of conventional techniques including Patent Literature 40 which is the unpublished earlier application, the surface tension of a water absorbing agent is decreased, and this adversely increases a returned liquid amount in absorbent articles.

CITATION LIST

Patent Literature

[Patent Literature 1]
  Specification of European Patent No. 1957188
[Patent Literature 2]
  Specification of U.S. Pat. No. 7,265,190

[Patent Literature 3]
  Japanese Patent Application Publication Tokukai No. 2005-162834
[Patent Literature 4]
  Specification of U.S. Pat. No. 6,710,141
[Patent Literature 5]
  Specification of U.S. Pat. No. 7,091,253
[Patent Literature 6]
  Pamphlet of International Publication No. 92/18171
[Patent Literature 7]
  Specification of U.S. Pat. No. 5,624,967
[Patent Literature 8]
  Pamphlet of International Publication No. 2005/012406
[Patent Literature 9]
  Specification of U.S. Pat. No. 5,002,986
[Patent Literature 10]
  Specification of U.S. Pat. No. 6,939,914
[Patent Literature 11]
  Specification of U.S. Pat. No. 5,124,188
[Patent Literature 12]
  Specification of European Patent No. 0595803
[Patent Literature 13]
  Specification of European Patent No. 0450922
[Patent Literature 14]
  Pamphlet of International Publication No. 91/15368
[Patent Literature 15]
  Specification of U.S. Pat. No. 5,154,713
[Patent Literature 16]
  Specification of U.S. Pat. No. 5,314,420
[Patent Literature 17]
  Specification of U.S. Pat. No. 5,399,591
[Patent Literature 18]
  Specification of U.S. Pat. No. 5,451,613
[Patent Literature 19]
  Specification of U.S. Pat. No. 5,462,972
[Patent Literature 20]
  Pamphlet of International Publication No. 95/02002
[Patent Literature 21]
  Pamphlet of International Publication No. 2005/063313
[Patent Literature 22]
  Pamphlet of International Publication No. 94/022502
[Patent Literature 23]
  Specification of U.S. Pat. No. 4,703,067
[Patent Literature 24]
  Pamphlet of International Publication No. 97/017397
[Patent Literature 25]
  Pamphlet of International Publication No. 00/052087
[Patent Literature 26]
  Specification of U.S. Pat. No. 6,107,358
[Patent Literature 27]
  Specification of U.S. Pat. No. 5,856,370
[Patent Literature 28]
  Specification of U.S. Pat. No. 5,985,944
[Patent Literature 29]
  Pamphlet of International Publication No. 2009/062902
[Patent Literature 30]
  Specification of US Patent Application Publication No. 2007/0225422
[Patent Literature 31]
  Japanese Patent Application Publication Tokukaihei No. 1-318021 (1989)
[Patent Literature 32]
  Pamphlet of International Publication No. 2011/078298
[Patent Literature 33]
  Specification of European Patent No. 1521601
[Patent Literature 34]
  Specification of U.S. Pat. No. 6,562,879
[Patent Literature 35]
  Specification of US Patent Application Publication No. 2005/0209352
[Patent Literature 36]
  Japanese Patent Application Publication Tokukaisho No. 63-105064 (1988)
[Patent Literature 37]
  Specification of U.S. Pat. No. 8,017,549
[Patent Literature 38]
  Pamphlet of International Publication No. 2005/075070
[Patent Literature 39]
  International Publication No. 2011/040472
[Patent Literature 40]
  Pamphlet of International Application No. PCT/JP2012/058515

SUMMARY OF INVENTION

Technical Problem

An object of the present invention is (i) to provide a particulate water absorbing agent that is excellent in water absorption physical properties, particularly in water absorbing speed and has a great bulk specific gravity and (ii) to provide a method for producing the particulate water absorbing agent.

Solution to Problem

The inventors of the present invention found that, only in a case where a surfactant which has an HLB of 10 or less is added by a specific amount, it is possible to obtain a water absorbing agent having a high bulk specific gravity without impairing water absorption physical properties such as a liquid permeability and a water absorbing speed. Further, the inventors of the present invention found it necessary to carry out a particular step in order to sufficiently bring about an effect of the present invention. Based on these findings, the inventors of the present invention have accomplished the present invention.

That is, a method of the present invention for producing a water absorbing agent includes: a surfactant adding step of adding a surfactant whose HLB is 10 or less, the surfactant adding step being the step of adding a dispersion liquid, which contains the surfactant equivalent to 30 parts by weight to 150 parts by weight (i.e., 30 mass ppm to 150 mass ppm relative to a mass of water absorbent resin), relative to 1000000 parts by weight of a water absorbent resin solid content, and the surfactant adding step being carried out after a drying step, and in a case where a water-soluble polyvalent metal salt adding step is carried out after the drying step, the surfactant adding step being carried out after the water-soluble polyvalent metal salt adding step.

Moreover, a water absorbing agent of the present invention is a water absorbing agent including a polyacrylic acid (salt)-based water absorbent resin as a main component, the water absorbing agent having a Hausner ratio of less than 1.18 and a water absorbing speed (FSR) of 0.25 [g/g/s] or more.

Further, a water absorbing agent of the present invention is a water absorbing agent including a polyacrylic acid (salt)-based water absorbent resin as a main component, the water absorbing agent having a moisture content of 3.0 mass % to 6.0 mass % or further including a liquid permeability improving agent, and the water absorbing agent further including 30 parts by weight to 150 parts by weight (i.e., 30 mass ppm to 150 mass ppm relative to a mass of water absorbent resin) of a surfactant, whose HLB is 10 or less, relative to 1000000 parts by weight of a water absorbent resin solid content.

Advantageous Effects of Invention

According to the method of the present invention for producing the water absorbing agent, it is possible to heighten a bulk specific gravity of the water absorbing agent without impairing water absorption physical properties such as a water absorbing speed. Therefore, it is unnecessary to carry out vibrational filling when the water absorbing agent is fed in a container for transportation or the like. This inhibits a crack and the like of the water absorbing agent which may be caused for filling in the container, and it is therefore possible to produce a high performance absorbent body.

DESCRIPTION OF EMBODIMENTS

The following description will discuss details of a water absorbing agent according to the present invention and a method for producing the water absorbing agent. Note, however, that the scope of the present invention is not limited to the following descriptions, and the present invention may be appropriately modified and worked in a manner other than examples described below, to the extent of being not contrary to the purpose of the present invention. Specifically, the present invention is not limited to the embodiments below, but can be variously altered by a skilled person in the art within the scope of the claims. An embodiment derived from a proper combination of technical means disclosed in respective different embodiments is also encompassed in the technical scope of the present invention.

[1] Term Definitions (1-1) "Water Absorbing Agent"

The term "water absorbing agent" in the present invention indicates an aqueous-liquid-absorbing gelatinizer whose main component is a water absorbent resin. In particular, a particulate aqueous-liquid-absorbing gelatinizer is referred to as "particulate water absorbing agent". A content of a water absorbent resin in the water absorbing agent is preferably 70 wt % to 100 wt %, further 85 wt % to 100 wt %, 90 wt % to 100 wt %, and an upper limit is 99 wt % or less, further 97 wt % or less.

(1-2) "Water Absorbent Resin"

The "water absorbent resin" of the present invention indicates a water-swelling and water-insoluble polymer gelatinizer. Note that "water-swelling" indicates that CRC (water absorption capacity without load) defined in ERT441.2-02 is 5 g/g or higher, and "water-insoluble" indicates that Ext (water soluble component) defined in ERT470.2-02 is 0 mass % to 50 mass %.

The water absorbent resin can be designed as appropriate in accordance with its purpose of use, and is not limited to a particular one. The water absorbent resin is preferably a hydrophilic crosslinked polymer which has been obtained by crosslinking and polymerizing unsaturated monomers each of which has a carboxyl group. Moreover, the water absorbent resin is not limited to a form in which the water absorbent resin is wholly (i.e., 100 mass %) a polymer, and can be a water absorbent resin composition that contains an additive and the like within a range in which the above described performance is maintained.

The water absorbent resin may be surface-crosslinked or not, is not limited to a particular form, may have a sheet form, a fiber form, a powder form, a film form, and a gel form, or the like form. These water absorbent resins are collectively referred to as "water absorbent resin". The water absorbent resin is preferably in the powder form.

(1-3) "Polyacrylic Acid (Salt)-Based Water Absorbent Resin"

The "polyacrylic acid (salt)-based water absorbent resin" of the present invention indicates a crosslinked polymer that arbitrarily contains a graft component and also contains, as a main component, acrylic acid and/or salt thereof (hereinafter, referred to as "acrylic acid (salt)") as a repeating unit. Specifically, "polyacrylic acid (salt)-based water absorbent resin" indicates a polymer that contains preferably 30 mol % to 100 mol % of acrylic acid (salt) as a monomer except a crosslinking agent.

(1-4) "EDANA" and "ERT"

"EDANA" is an abbreviation for "European Disposables and Nonwovens Associations", and "ERT" is an abbreviation for "EDANA Recommended Test Methods" which is a European standard (which is substantially an international standard) method for measuring water absorbent resin. In the present invention, measurement is carried out according to the ERT original copy (revised in 2002, publicly known document), unless otherwise noted.

(A) "CRC" (ERT441.2-02)

"CRC" is an abbreviation for Centrifuge Retention Capacity, and means water absorption capacity (hereinafter, also referred to as "water absorption capacity", and being synonymous with "absorbency") without load of the water absorbent resin. Specifically, "CRC" is water absorption capacity (unit; [g/g]) measured when 0.200 g of a water absorbent resin in a nonwoven fabric bag (i) has been soaked (freely swollen) in a large excess of a 0.9 mass % sodium chloride aqueous solution for 30 minutes and (ii) then is drained by a centrifugal separator.

(b) "AAP" (ERT442.2-02)

"AAP" is an abbreviation for Absorbency Against Pressure, and means water absorption capacity under load of the water absorbent resin. Specifically, "AAP" is water absorption capacity (unit; [g/g]) measured when 0.900 g of a water absorbent resin has swollen a large excess of a 0.9 mass % sodium chloride aqueous solution for 1 hour under a load of 2.06 kPa (0.3 psi, 21 [g/cm$^2$]). Note that Absorption Under Pressure in ERT442.2-02 is substantially identical with AAP. Moreover, measurement may be carried out under conditions where the load is changed to 4.83 kPa (0.7 psi, 50 [g/cm$^2$]).

(c) "PSD" (ERT420.2-02)

"PSD" is an abbreviation for Particle Size Distribution, and means a particle size distribution of the water absorbent resin which is measured by sieve classification.

Moreover, a mass average particle diameter (D50) and a particle diameter distribution width of the water absorbent resin are measured according to a method similar to a method disclosed in US Patent Application Publication No. 2006-204755, "(1) Average Particle Diameter and Distribution of Particle Diameter".

(1-5) "Liquid Permeability"

Flow of a liquid, which flows between water absorbent resin particles swollen under a load or without load, is referred to as "liquid permeability". Typical methods for measuring the "liquid permeability" encompass SFC (Saline Flow Conductivity) and GBP (Gel Bed Permeability).

The "SFC (saline flow conductivity)" indicates a liquid permeability of a 0.69 wt % of physiological saline solution relative to water absorbent resin particles under a load of 2.07 kPa, and is measured in accordance with an SFC testing method described in the specification of U.S. Pat. No. 5,669,894.

The "GBP" indicates a liquid permeability of a 0.69 wt % of physiological saline solution relative to water absorbent resin particles under a load or being free swollen, and is measured in accordance with a GBP testing method described in the pamphlet of International Publication No. 2005/016393.

(1-6) Others

In this specification, a range "X to Y" means "X or more (higher) and Y or less (lower)". Moreover, "t (ton)", which is a unit of weight, means "metric ton", "weight" is synonymous with "mass", "wt %" is synonymous with "mass %", and "parts by weight" is synonymous with "parts by mass". Moreover, unless otherwise noted, "ppm" means "ppm by weight" or "ppm by mass". Further, " . . . acid (salt)" means " . . . acid and/or salt thereof", and "(meth) acrylic" means "acrylic and/or methacrylic".

[2] Method for Producing Particulate water absorbing agent (2-1) Polymerization Step (Monomer)

A water absorbent resin, which is used as a main component in the particulate water absorbing agent that is obtained by the producing method of the present invention, is a polyacrylic acid (salt)-based water absorbent resin, and is a water-swelling and water-insoluble crosslinked polymer. This water-swelling and water-insoluble crosslinked polymer contains an acrylic acid (salt) as a monomer in a repeating unit (except for crosslinking agent later described), in an amount of preferably 30 mol % to 100 mol %, more preferably 50 mol % to 100 mol %, still more preferably 70 mol % to 100 mol %, and particularly preferably 90 mol % to 100 mol %, or substantially 100 mol %.

An acid group of a monomer before or after polymerization is preferably neutralized. A neutralized salt is preferably monovalent salt, more preferably alkali metal salt or ammonium salt, still more preferably alkali metal salt, and particularly preferably, sodium salt. It is preferable that, as the sodium salt, 0 mol % to 100 mol %, preferably 20 mol % to 100 mol %, more preferably 50 mol % to 99 mol %, and still more preferably 60 mol % to 90 mol % of the acid group be neutralized. The neutralization can be carried out before polymerization, can be carried out on a hydrogel after polymerization, or both the neutralizations can be carried out. Preferably, the neutralization is carried out before polymerization.

(Other Monomer and Crosslinking Agent)

According to the present invention, an unsaturated monomer other than acrylic acid (salt) (hereinafter, referred to as "other monomer") can be used in an amount of 0 mol % to 70 mol % of entire monomer components.

Examples of the "other monomer" encompass hydrophilic unsaturated monomers such as methacrylic acid, maleic acid (anhydride), fumaric acid, crotonic acid, itaconic acid, vinyl sulfonic acid, 2-(meth)acrylamide-2-methylpropane sulfonic acid, (meth)acryloxyalkane sulfonic acid, N-vinyl-2-pyrrolidone, N-vinylacetamide, (meth)acrylamide, N-isopropyl(meth)acrylamide, N,N-dimethyl(meth)acrylamide, 2-hydroxyethyl(meth)acrylate, methoxypolyethylene glycol (meth)acrylate, polyethylene glycol(meth)acrylate, and salts thereof.

The crosslinking agent that can be used in the present invention is not limited to a particular one, and can be, for example, the following compounds: (i) compounds, each of which has at least two polymerizable double bonds per molecule, such as N,N'-methylenebisacrylamide, (poly)ethylene glycol di(meth)acrylate, (poly)propylene glycol di(meth)acrylate, (polyoxyethylene)trimethylolpropane tri (meth)acrylate, trimethylolpropanedi(meth)acrylate, polyethylene glycol di(β-acryloyloxypropionate), trimethylolpropane tri(β-acryloyloxypropionate), and poly(meth) allyloxyalkane; and (ii) compounds each of which can form a covalent bond by reaction with a carboxyl group, such as (a) polyglycidyl ethers such as ethylene glycol diglycidyl ether and (b) polyols such as ethylene glycol, polyethylene glycol, glycerin, and sorbitol.

The crosslinking agent can be used solely or two or more crosslinking agents in combination. Note that, in a case where the crosslinking agent is used, it is preferable to use the compound that has at least two polymerizable double bonds per molecule, in consideration of an absorption performance etc. of a resultant particulate water absorbing agent. A used amount of the crosslinking agent is preferably 0 mol % to 5 mol %, and more preferably 0.001 mol % to 2 mol % relative to a monomer, from the viewpoint of physical properties.

According to the present invention, if needed, it is possible to add, to the monomer, preferably 5 mass % or lower, and more preferably 1 mass % or lower of a foaming agent, a deodorant agent, an antibacterial agent, a plasticizer, a perfume, a pigment, a dye, a hydrophilic short fiber, inorganic powder such as silicon dioxide or titanium oxide, a thermoplastic resin such as polyethylene or polypropylene, a chain transfer agent such as hypophosphorous acid (salt), or the like.

Further, it is possible to have an arrangement in which a water absorbent resin or a water-soluble resin is present in the monomer at initiation of polymerization or in a water-containing gel-like crosslinked polymer (hereinafter, referred to as "hydrogel") during or after the polymerization. Specifically, it is possible to have an arrangement in which polysaccharide such as starch or cellulose or a derivative thereof, polyvinyl alcohol, or the like is present in an amount of preferably 0 mass % to 50 mass %, and more preferably 0.1 mass % to 30 mass %. A mixture with such a graft polymer or other polymer can be referred to as "water absorbent resin composition". Note, however, that, in the present invention, the mixture with such a graft polymer or other polymer is referred to as "water absorbent resin" or "polyacrylic acid (salt)-based water absorbent resin".

(Polymerization Method)

The polymerization carried out in the present invention is spray polymerization or drop polymerization (in a gaseous phase), aqueous solution polymerization, or reverse phase suspension polymerization (in a hydrophobic organic solvent), from the viewpoint of a water absorption performance of a resultant particulate water absorbing agent, easy polymerization control, and the like. These polymerizations can be carried out in an air atmosphere. However, from the viewpoint of improvement in color tone of the particulate water absorbing agent, the polymerizations are preferably carried out in an atmosphere of inert gas such as nitrogen or argon (for example, with an oxygen concentration of 1 volume % or lower). Further, it is preferable that dissolved oxygen in the monomer be sufficiently replaced by inert gas (so that an amount of the dissolved oxygen is, for example, less than 1 mg/L).

According to the present invention, the monomer is preferably used in a solution form obtained with water or with a mixed solvent of water and a hydrophilic solvent, and particularly preferably, in an aqueous solution form. In this case, a monomer concentration is preferably 20 mass % to 80 mass %, more preferably 30 mass % to 70 mass %, and still more preferably 40 mass % to 60 mass %. Note that an excessively high monomer concentration tends to lower a water absorption capacity, and is therefore not preferable.

The aqueous solution polymerization is a method in which a monomer aqueous solution is polymerized without use of a dispersion solvent such as a hydrophobic organic solvent. This aqueous solution polymerization is a form of polymerization disclosed in, for example, U.S. Pat. Nos. 4,625,001, 4,873,299, 4,286,082, 4,973,632, 4,985,518, 5,124,416, 5,250,640, 5,264,495, 5,145,906, 5,380,808, and the like, European Patents Nos. 0811636, 0955086, 0922717, 1178059, 1711541, 1799721, and the like.

The reverse phase suspension polymerization is a method in which polymerization is carried out by suspending a monomer aqueous solution in a hydrophobic organic solvent. The reverse phase suspension polymerization is a form of polymerization disclosed in, for example, U.S. Pat. Nos. 4,093,776, 4,367,323, 4,446,261, 4,683,274, 5,244,735, and the like. Note that, in the polymerization of the present invention, the monomers, the crosslinking agents, the polymerization initiators, and other additives disclosed in the above Patent Literatures can also be used. The drop or spray polymerization is a polymerization method carried out by spraying or dropping a monomer aqueous solution in a gaseous phase as disclosed in, for example, the pamphlet of International Publication No. 2011/026876.

(Polymerization Initiator)

A polymerization initiator used in the present invention is selected as appropriate in accordance with a form of polymerization, and is not limited to a particular one. Examples of the polymerization initiator encompass a photolytic polymerization initiator, a pyrolytic polymerization initiator, and a redox polymerization initiator. A used amount of the polymerization initiator is preferably 0.0001 mol % to 1 mol %, more preferably 0.001 mol % to 0.5 mol %, relative to the monomer.

Examples of the photolytic polymerization initiator encompass a benzoin derivative, a benzil derivative, an acetophenone derivative, a benzophenone derivative, an azo compound, and the like.

Examples of the pyrolytic polymerization initiator encompass persulfates such as sodium persulfate, potassium persulfate, and ammonium persulfate; peroxides such as hydrogen peroxide, t-butyl peroxide, and methyl ethyl ketone peroxide; azo compounds such as an azonitrile compound, an azoamidine compound, a cyclic azoamidine compound, an azoamide compound, an alkylazo compound, 2,2'-azobis(2-amidinopropane)dihydrochloride, and 2,2'-azobis[2-(2-imidazoline-2-yl)propane]dihydrochloride; and the like.

Examples of the redox polymerization initiator encompass a system using a combination of (i) the persulfate, the peroxide, or the like and (ii) a reducing compound such as L-ascorbic acid, sodium hydrogen sulfite, or the like.

Alternatively, the photolytic polymerization initiator can be used in combination with the pyrolytic polymerization initiator.

(Surfactant, Dispersing Agent)

In the present invention, (i) a surfactant such as an anionic surfactant, a nonionic surfactant, a cationic surfactant, or an amphoteric surfactant or (ii) a dispersing agent can be used in polymerization. The surfactant or the dispersing agent is not limited to a particular one. Examples of the anionic surfactant encompass fatty acid sodiums such as mixed fatty acid sodium soap and sodium stearate, higher alcohol sodium sulfate, sodium alkyl sulfate, alkyl benzene sulfonate, and the like. Examples of the cationic surfactant and the amphoteric surfactant encompass alkylamines, alkylbetaine, and the like. The nonionic surfactant preferably has an HLB of greater than 10. Such a nonionic surfactant is equivalent to a nonionic surfactant that has an HLB of greater than 10 and is exemplified as a water-soluble dispersing agent in preparing a dispersion liquid of a nonionic surfactant whose HLB is 10 or less (which is later described). Here, the HLB is defined by a value calculated based on a Griffin formula and may be, depending on circumstances, a catalog value or a value calculated by another method.

Examples of the dispersing agent encompass ethyl cellulose, ethyl hydroxyethyl cellulose, and the like.

A used amount of the surfactant or the dispersing agent is determined as appropriate in accordance with a form of polymerization to an extent of being not contrary to the effect of the present invention. In general, the used amount is preferably more than 0 and 30 parts by mass or less, and is more preferably more than 0 and 5 parts by mass or less, relative to 100 parts by mass of entire monomer components including polymerizable monomers and crosslinkable monomers.

(Organic Solvent in Reverse Phase Suspension Polymerization)

In a case where the reverse phase suspension polymerization is carried out, an organic solvent to be used is not limited to a particular one, provided that the organic solvent is poorly water soluble and inert with respect to polymerization. Examples of the organic solvent encompass aliphatic hydrocarbons such as n-pentane, n-hexane, n-heptane, and n-octane, alicyclic hydrocarbons such as cyclohexane and methylcyclohexane, aromatic hydrocarbons such as benzene, toluene, and xylene, and the like. Among these, n-hexane, n-heptane, and cyclohexane are particularly preferable, from the viewpoint of stability in industrial availability, quality, and the like. A used amount of the organic solvent is preferably 0.5 times to 10 times, more preferably 0.6 times to 5 times as large, by mass, as that of a polymerizable monomer aqueous solution.

(2-2) Gel-Grain Refining Step (Optional)

The hydrogel obtained by the polymerization step can be directly dried. However, in a case of aqueous solution polymerization, it is preferable that a hydrogel during or after polymerization is gel-crushed with use of a gel crusher (such as kneader or meat chopper, etc.) or the like, and the hydrogel thus grain-refined (hereinafter, referred to as "particulate hydrogel") is dried. In this case, grain refining of the hydrogel is carried out by a predetermined method so that a mass average particle diameter (D50) (defined by wet sieve classification) of the particulate hydrogel becomes preferably 0.1 mm to 50 mm, more preferably 0.2 mm to 10 mm, and still more preferably 0.5 mm to 5 mm.

Note that a form of the water absorbent resin used in the particulate water absorbing agent according to the present invention is not limited to a particular one and can be, for example, in an arbitrary form such as a granule form, a powder form, a flake form, or a fiber form. The grain refining can be carried out any of various methods such as a method in which gel-crushing is carried out with the use of a screw extruder having an arbitrarily-shaped porous structure.

(2-3) Drying Step

In the drying step, a hydrogel or a particulate hydrogel which has been obtained in the polymerization step or in the gel-grain refining step is dried so as to obtain a dried polymer. Drying (i) may be carried out simultaneously with polymerization or surface crosslinking, or (ii) may be carried out separately, or (iii) may be carried out (a) simultaneously with polymerization or surface crosslinking and (b) also separately. Preferably, the drying step is carried out after polymerization and before surface crosslinking. A drying method here is not limited to a particular one and can be, for example, various drying methods such as drying by heating, hot air drying, drying under reduced pressure, fluidized-bed drying, infrared drying, microwave drying, drying with a drum dryer, dehydration by azeotropy with a hydrophobic organic solvent, and high humidity drying with hot moisture vapor.

Among these, a drying method carried out by contact with a gas is preferable, and a dew point of the gas to be used is preferably 40° C. to 100° C., and more preferably 50° C. to 90° C.

In the drying step of the present invention, a drying temperature is not limited to a particular one and is, for example, preferably 50° C. to 300° C., and from the viewpoint of improvement in water absorption capacity, more preferably 100° C. to 250° C., still more preferably 120° C. to 230° C., and particularly preferably 150° C. to 200° C. Note that, in a case where the drying temperature is 100° C. or lower, the azeotropic dehydration or the drying under reduced pressure is preferable. Moreover, a drying time is determined as appropriate and is not limited to a particular time, and is, for example, preferably 10 seconds to 5 hours, and more preferably 1 minute to 2 hours.

In a case where the form of polymerization of the present invention is the polymerization in an aqueous solution, from the viewpoint of physical properties of an obtained particulate water absorbing agent, easy pulverization, and the like, a solid content (defined in (5-3) Solid Content and Moisture Content) of a dried polymer (water absorbent resin) after drying is preferably 80 mass % or higher, more preferably 85 mass % or higher, still more preferably 90 mass % or higher and particularly preferably 92 mass % to 98 mass %, and the dried polymer thus dried is then preferably further subjected to surface crosslinking.

In a case where the polymerization form of the present invention is the reverse phase suspension polymerization, a hydrogel obtained during or after polymerization can be dried by, for example, carrying out azeotropic dehydration in a state where the hydrogel is dispersed in an organic solvent of hydrocarbon or the like. The solid content after drying is 60 mass % or higher, preferably 70 mass % or higher, more preferably 80 mass % or higher, still more preferably 85 mass % or higher, further still more preferably 90 mass % or higher, particularly preferably 92 mass % to 98 mass %, and most preferably 93 mass % to 97 mass %. It is preferable that surface crosslinking of the hydrogel is carried out during the drying step (e.g., with the solid content of 60 mass % to 90 mass %). Note that, after the drying, the hydrogel can be separated from the organic solvent by decantation or evaporation, and can be then further dried if needed.

(2-4) Pulverizing Step, Classification Step

In this step, a dried polymer (i.e., dried hydrogel) obtained in the drying step is pulverized (pulverizing step) if needed, and is further classified (classification step) so as to control a particle size, so that water absorbent resin particles are obtained. The pulverization and the classification can be carried out according to, for example, the method disclosed in International Publication No. 2004/69915.

The water absorbent resin particles (i.e., the water absorbent resin before surface crosslinking) are preferably controlled to have a particular range of particle size by pulverizing, classification, and blending after classification, from the viewpoint of improvement in water absorption capacity under load (AAP) and liquid permeability (SFC, GBP). The pulverizing, classification, and blending after classification can be, if needed, carried out with respect to the water absorbent resin after surface crosslinking or to the ultimate particulate water absorbing agent.

A method for adjusting the particle size can be, for example, (i) a method in which the particle size is controlled to be in an intended range by controlling pulverizing conditions such as a clearance and a throughput of the crusher, a mesh size of a sieve used in the classification step, and the like or (ii) a method in which water absorbent resin particles having different particle sizes are mixed. In the adjusting method, it is necessary to control each of all the mass average particle diameter, the logarithmic standard deviation of particle size distribution, and contents of coarse particles and fine particles to fall within a predetermined range. Fine powder (e.g., which have passed through 150 μm of a sieve) after classification can be removed or recycled. Moreover, coarse particles (e.g., which have not passed through 850 μm of a sieve) after classification can be removed or re-pulverized.

The predetermined range is the mass average particle diameter (D50) which is 200 μm to 600 μm, preferably 250 μm to 550 μm, and more preferably 350 μm to 500 μm. Moreover, the logarithmic standard deviation (σζ) of particle size distribution is 0.20 to 0.50, preferably 0.25 to 0.45, and more preferably 0.30 to 0.35. Further, a ratio of coarse particles having a particle diameter of 850 μm or larger (defined by JIS-standard sieve) is preferably as low as possible, and is in general 0 mass % to 5 mass %, preferably 0 mass % to 3 mass %, and more preferably 0 mass % to 1 mass %. A ratio of fine particles having a particle diameter of smaller than 150 μm (defined by JIS-standard sieve) is also preferably as low as possible, and is in general 0 mass % to 5 mass %, preferably 0 mass % to 3 mass %, and more preferably 0 mass % to 1 mass %.

(2-5) Surface Crosslinking Step

In this step, surface crosslinking is carried out with respect to water absorbent resin particles obtained through the pulverizing step and the classification step, in order to improve a water absorption capacity under load (AAP) of a resultant water absorbent resin. Note that the "surface crosslinking" indicates forming crosslinks on or in the vicinity of a surface of the water absorbent resin particles. Moreover, "on or in the vicinity of a surface" means, in general, (i) a surface layer part having a thickness of several tens of micrometers or less or (ii) a surface layer part having a thickness of 1/10 or less of a whole thickness. Note, however, that the thickness is determined as appropriate in accordance with purposes. The water absorbent resin used in the particulate water absorbing agent of the present invention can be obtained by surface-crosslinking the water absorbent resin particles which have been obtained by the above steps (2-1) through (2-4).

A method of the surface crosslinking is not limited to a particular one and can be, for example, (i) a method in which monomers are polymerized on a surface of the water absorbent resin particles or (ii) a method in which radical crosslinking is carried out on a surface of the water absorbent resin particles with the use of a polymerization initiator (e.g., persulfate). Note, however, that it is particularly preferable to employ a method in which crosslinking is carried out on a surface of the water absorbent resin particles with the use of a surface crosslinking agent. In this case, the surface crosslinking step includes a mixing step of mixing with the surface crosslinking agent, a heating treatment step of heating treatment the mixture, and, if needed, a cooling step.

(Surface Crosslinking Agent)

The surface crosslinking agent used in the present invention is not limited to a particular one and can be, for example, an oxazoline compound (see U.S. Pat. No. 6,297,319), a vinyl ether compound (see U.S. Pat. No. 6,372,852), an epoxy compound (see U.S. Pat. No. 625,488), an oxetane compound (see U.S. Pat. No. 6,809,158), a polyhydric alcohol compound (see U.S. Pat. No. 4,734,478), a polyamide polyamine-epihalo adduct (see U.S. Pat. Nos. 4,755,562 and 4,824,901), a hydroxyacrylamide compound (see U.S. Pat. No. 6,239,230), an oxazolidinone compound (see U.S. Pat. No. 6,559,239), a bis or poly-oxazolidinone compound (see U.S. Pat. No. 6,472,478), a 2-oxotetrahydro-1,3-oxazolidine compound (see U.S. Pat. No. 6,657,015), an alkylene carbonate compound (see U.S. Pat. No. 5,672,633), and the like, each of which is used solely or two or more of which are used in combination.

Further, it is possible to use the surface crosslinking agent in combination with water-soluble polyvalent metal cation such as aluminum salt (see U.S. Pat. Nos. 6,605,673, and 6,620,899), or it is possible to use the surface crosslinking agent in combination with alkali metal salt (see US Patent Application Publication No. 2004/106745), organic acid or inorganic acid (see U.S. Pat. No. 5,610,208), or the like. Alternatively, the surface crosslinking can be polymerization of monomers on a surface of the water absorbent resin (see US Patent Application Publication No. 2005/48221).

Among these, it is preferable to use an organic surface crosslinking agent, in particular, a covalent bonding surface-crosslinking agent. Specifically, it is preferable to use at least one of a polyhydric alcohol compound, a polyvalent epoxy compound, a polyhydric amine compound or salt thereof, and an alkylene carbonate compound. In general, each of these compounds causes a surface to be hydrophilic, and therefore, allows efficient application of the producing method of the present invention.

Concrete examples of surface crosslinking agents encompass polyhydric alcohol compounds such as (di, tri, tetra, poly)ethylene glycol, (di, poly)propylene glycol, 1,3-propanediol, 2,2,4-trimethyl-1,3-pentanediol, (poly)glycerin, 2-butene-1,4-diol, 1,4-butanediol, 1,3-butanediol, 1,5-pentanediol, 1,6-hexanediol, trimethylolpropane, di or triethanolamine, pentaerythritol, and sorbitol; epoxy compounds such as (poly)ethylene glycol diglycidyl ether, (di, poly) glycerol polyglycidyl ether, (di, poly)propylene glycol diglycidyl ether, and glycidol; polyvalent oxazoline compounds such as 1,2-ethylenebisoxazoline; alkylene carbonate compounds such as 1,3-dioxolane-2-one; mono-oxazolidinone compounds or polyvalent oxazolidinone compounds such as 2-oxazolidinone; and oxetane compounds.

Among the above surface crosslinking agents, from the viewpoint of physical properties of a particulate water absorbing agent, it is preferable to use a dehydration reactive surface-crosslinking agent selected from among the polyhydric alcohol compound, the alkylene carbonate compound, the oxazolidinone compound, and the oxetane compound. In particular, it is preferable to use at least one selected from among the polyhydric alcohol compound, the alkylene carbonate compound, and the oxazolidinone compound, and if needed, other surface crosslinking agent(s). Note that, here, the dehydration reactive surface-crosslinking agent indicates a crosslinking agent for forming crosslinks by dehydration reaction with a carboxyl group of polyacrylic acid (salt).

Surface crosslinking agents other than the above dehydration reactive surface-crosslinking agent can be, for example, an ion-reactive surface crosslinking agent such as polyvalent metal salt, and a ring-opening-reactive surface crosslinking agent such as an epoxy compound crosslinking agent. These surface crosslinking agents can be used solely or in combination.

The ion reaction surface crosslinking agent can be a polyvalent metal compound such as aluminum sulfate that contains a water-soluble polyvalent metal cation.

A used amount of the surface crosslinking agent is preferably 0.01 part by mass to 10 parts by mass, and more preferably 0.5 part by mass to 5 parts by mass, relative to 100 parts by mass of the water absorbent resin. In a case where the used amount of the surface crosslinking agent is less than 0.01 part by mass, a liquid permeability may decrease, and such an amount is therefore not preferable. On the other hand, in a case where the used amount of the surface crosslinking agent is more than 10 parts by mass, a water absorption capacity may extremely decrease, and such an amount is therefore not preferable.

Note that the surface crosslinking agent can be used solely or two or more of the surface crosslinking agents can be used in combination.

(Solvent)

When the water absorbent resin particles are mixed with the surface crosslinking agent, the surface crosslinking agent can be solely mixed. Note, however, that it is preferable to mix the surface crosslinking agent in a solution form, and it is particularly preferable to use water as a solvent. In a case where a total used amount of water is 1 part by mass to 10 parts by mass relative to 100 parts by mass of the water absorbent resin particles, a surface crosslinking agent aqueous solution sufficiently permeates the surface of the water absorbent resin. Accordingly, multiple surface-crosslinked layers are formed which have appropriate thickness and density.

When the surface crosslinking agent is mixed with the water absorbent resin particles, if needed, a hydrophilic organic solvent can be used as a solvent. Examples of the hydrophilic organic solvent encompass lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and alkoxy polyethylene glycol; amides such as N,N-dimethylformamide; sulfoxides such as dimethyl sulfoxide; and the like. A used amount of the hydrophilic organic solvent varies depending on a type, a particle size, and the like of the water absorbent resin particles, and is preferably 20 parts by mass or less, and more preferably in a range of 0.1 part by mass to 10 parts by mass, relative to 100 parts by mass of a solid content of the water absorbent resin particles.

Moreover, the surface crosslinking agent can coexist with water-insoluble fine particle powder or a surfactant to an extent of being not contrary to the effect of the present invention. An amount of such water-insoluble fine particle powder or surfactant can be, for example, more than 0 part by weight and 10 parts by weight or less, preferably more than 0 part by weight and 5 parts by weight or less, and more preferably more than 0 part by weight and 1 part by weight or less. The surfactant used here is equivalent to the surfactant used in the polymerization step.

(Surface Crosslinking Method)

A method for mixing the water absorbent resin particles with the surface crosslinking agent is not limited to a particular one, and is preferably a method in which a surface crosslinking agent, which is dissolved in water and/or a hydrophilic organic solvent, is mixed by direct spraying or direct dropping onto the water absorbent resin particles.

A mixer used to mix the water absorbent resin particles with the surface crosslinking agent preferably has a great mixing power so as to uniformly and reliably mix the water absorbent resin particles with the surface crosslinking agent. The mixer is not limited to a particular one, and examples of the mixer encompass a cylindrical mixer, a double walled conical mixer, a V-shaped mixer, a ribbon mixer, a screw mixer, a flow furnace rotary disk type mixer, an airflow mixer, a double-arm kneader, an internal mixer, a pulverizing kneader, a rotary mixer, a screw extruder, a turbulizer, and the like.

When the surface crosslinking agent is mixed with the water absorbent resin particles, temperatures of the water absorbent resin particles, the surface crosslinking agent aqueous solution, and the mixture thereof are preferably 10° C. to 200° C., and more preferably 20° C. to 100° C. Moreover, a mixing time is preferably 1 second to 1 hour, and more preferably 5 seconds to 10 minutes.

The mixture of the water absorbent resin particles and the surface crosslinking agent is preferably heated for causing a crosslinking reaction. A heating temperature can be selected as appropriate, and a heating medium temperature is preferably in a range of 150° C. to 250° C., and more preferably in a range of 180° C. to 210° C. A heating time is preferably 1 minute to 2 hours, and a preferable example of a combination of the heating temperature and the heating time is 0.1 to 1.5 hours at 180° C., 0.1 to 1 hour at 200° C., or the like. An atmospheric dew point in heating reaction can also be controlled as appropriate to approximately 0° to 100° C. in accordance with purposes with the use of, for example, a method disclosed in PCT/2013/072206 or PCT/2013/072207.

When the mixture of the water absorbent resin particles and the surface crosslinking agent is heated, the mixture can be heated in a still state or can be heated with the use of mixing means such as stirring. From the viewpoint of evenly heating the whole mixture, it is preferable to heat the mixture which is being mixed by stirring.

(2-6) Step of Adding Liquid Permeability Improving Agent

In this step, a liquid permeability improving agent is added to water absorbent resin particles after the drying step or to water absorbent resin particles after the surface crosslinking step. The liquid permeability improving agent in the present invention is a substance to improve a saline flow conductivity (SFC) of water absorbent resin particles after the liquid permeability improving agent adding step, as compared with the SFC of water absorbent resin particles before the liquid permeability improving agent adding step.

(Liquid Permeability Improving Agent)

The liquid permeability improving agent used in this step can be a water-soluble compound containing a polyvalent metal cation. A valence of the polyvalent metal cation is 2 or more (i.e., divalent or more), preferably 2 to 4 (i.e., divalent to tetravalent), and more preferably 3 (i.e., trivalent).

The water-soluble compound indicates a compound, 1 g or more, and preferably 10 g or more of which can be dissolved in 100 g of water (at 25° C.). The polyvalent metal compound containing the polyvalent metal cation as it is (i.e., mainly in a solid state) can be mixed with the water absorbent resin particles. Note, however, that it is preferable to mix an aqueous solution of the polyvalent metal compound with the water absorbent resin.

A polyvalent metal cationic element that can be used in the present invention is at least one metal selected from among main group metals and transition metals in groups 4 to 11, and is preferably one selected from among Mg, Ca, Ti, Zr, V, Cr, Mn, Fe, Co, Ni, Pd, Cu, Zn, Cd, and Al, more preferably Mg, Ca, Zn, and Al, and particularly preferably Al.

In the polyvalent metal compound containing a polyvalent metal cation, a counter anion is not limited in particular and can be organic or inorganic. Examples of such a polyvalent metal compound encompass water-soluble aluminum salts such as aluminium acetate, aluminum lactate, aluminum acrylate, aluminium chloride, polyaluminum chloride, aluminum sulfate, aluminum nitrate, bis-potassium aluminum sulfate, and bis-sodium aluminum sulfate; water-soluble alkaline earth metal salts such as calcium chloride, calcium nitrate, magnesium chloride, magnesium sulfate, and magnesium nitrate; transition metal salts such as zinc chloride, zinc sulfate, zinc nitrate, copper sulfate, cobalt chloride, zirconium chloride, zirconium sulfate, and zirconium nitrate; and the like. Among these, an aluminum compound is particularly preferable, and further, aluminum sulfate is preferable. It is possible to most preferably use hydrated crystal powder such as aluminum sulfate tetradecahydrate to octadecahydrate.

In a case where an organic acid polyvalent metal salt is used, an anion is preferably a base that corresponds to an acid such as anisic acid, benzoic acid, p-hydroxybenzoic acid, formic acid, valeric acid, citric acid, glycolic acid, glycerinic acid, glutaric acid, chloroacetic acid, chloropropionic acid, cinnamic acid, succinic acid, acetic acid, tartaric acid, lactic acid, pyruvic acid, fumaric acid, propionic acid, 3-hydroxypropionic acid, malonic acid, maleic acid, butyric acid, isobutyric acid, imidino acetic acid, malic acid, isothionic acid, methylmaleic acid, adipic acid, itaconic acid, crotonic acid, oxalic acid, salicylic acid, gluconic acid, gallic acid, sorbic acid, or fatty acid such as stearic acid. Among these, tartrate and lactate are preferable, and lactate such as aluminum lactate or calcium lactate is the most preferable.

As to a method for mixing the polyvalent metal cation, an aqueous solution containing the polyvalent metal cation is mixed with the water absorbent resin. In particular, a concentration of the polyvalent metal cation in the aqueous solution is 1 mass % to 60 mass %, further 10 mass % to 50 mass %. Furthermore, if needed, after mixing the polyvalent metal cation, a resultant mixture can be heated at approximately 40° C. to 150° C., further 60° C. to 100° C. A used amount of water is preferably 0.1 part by mass to 5 parts by mass, and still more preferably 0.5 part by mass to 3 parts by mass, relative to 100 parts by mass of the water absorbent resin.

Still more preferably, a polyhydric alcohol or α-hydroxycarboxylic acid is also used in combination in the mixing. Note that the polyhydric alcohol or α-hydroxycarboxylic acid is selected as appropriate from among the above described compounds. A preferable used amount of the polyhydric alcohol or α-hydroxycarboxylic acid is (i) smaller than that of water and (ii) 0 part by mass to 4 parts by mass, 0.01 part by mass to 3 parts by mass, further 0.1 part by mass to 0.5 part by mass, relative to 100 parts by mass of the water absorbent resin.

A used amount of the polyvalent metal compound (in terms of an amount of the polyvalent metal cation, e.g., in a case of aluminum salt, $Al^{3+}$ regardless of a kind of salt) falls within preferably a range of 0.001 part by mass to 1 part by mass, more preferably a range of 0.005 part by mass to 0.5 part by mass, further still more preferably a range of 0.01 part by mass to 0.2 part by mass, and particularly preferably a range of 0.02 part by mass to 0.1 part by mass, relative to 100 parts by mass of the water absorbent resin particles.

In a case where the polyvalent metal cation content in the particulate water absorbing agent is less than 0.001 part by mass relative to 100 parts by mass of the water absorbent resin, SFC may not be improved sufficiently. In a case where the content is more than 1 part by mass, AAP may significantly decrease.

(2-7) Surfactant Adding Step

In this step, a surfactant whose HLB is 10 or less is added to the water absorbent resin particles. This step is preferably carried out with respect to water absorbent resin particles after the drying step. In a case where the liquid permeability improving agent adding step is carried out, the surfactant adding step is preferably carried out after the liquid permeability improving agent adding step. Here, the HLB is calculated by the Griffin formula, and can be substituted by a catalog value or by a value calculated with another method.

An added amount of the surfactant (hereinafter, sometimes referred to as "specific surfactant") having an HLB of 10 or less is preferably 30 parts by mass to 150 parts by mass, more preferably 30 parts by mass to 100 parts by mass, and still more preferably 75 parts by mass to 100 parts by mass, relative to a solid content of the water absorbent resin used in this step, i.e., 1000000 parts by mass of the water absorbent resin. In a case where the added amount is less than 30 parts by mass, the effect of the present invention may not be sufficiently brought about. In a case where the added amount is more than 150 parts by mass, not only the effect of the present invention may not be brought about but also a surface tension of the absorbed liquid is decreased, and this unfavorably causes increase in returned liquid amount in a disposable diaper, etc.

A temperature of the water absorbent resin particles in this step is preferably 20° C. to 100° C., and more preferably 20° C. to 80° C. In a case where the temperature of the water absorbent resin particles is lower than 20° C., the effect of the present invention cannot be brought about, and therefore this is not preferable.

In this step, it is not necessary to particularly carry out heating and cooling, provided that dew condensation and the like do not occur. Moreover, an atmosphere is not limited in particular, and can be nitrogen or air.

(Surfactant Whose HLB is 10 or Less)

In the present invention, the surfactant whose HLB is 10 or less is essentially used. The HLB can be calculated by the Griffin method, and a surfactant is used whose range of HLB is essentially 0 to 10, preferably 1 to 8, more preferably 1 to 6, and particularly preferably 1 to 4.

In a case where an HLB of a surfactant is unknown, the HLB is measured as follows: i.e., a certain kind of oil is emulsified by the surfactant (if needed, a surfactant whose HLB is known is added), and the same kind of oil is emulsified by each of other surfactants whose HLBs are known and different. Then, the unknown HLB of the surfactant is determined to be an HLB which is of a known surfactant that caused the same emulsion state.

The surfactant whose HLB is 10 or less is preferably at least one compound selected from polyoxyethylene alkyl ether whose HLB is 10 or less, sorbitan fatty acid ester, polyoxyethylene sorbitan fatty acid ester, glycerine fatty acid ester, and sucrose fatty acid ester.

Specifically, examples of polyoxyethylene alkyl ether whose HLB is 10 or less encompass polyoxyethylene lauryl ether, polyoxyethylene stearyl ether, and polyoxyethylene oleyl ether; examples of sorbitan fatty acid ester encompass sorbitan monolaurate, sorbitan monopalmitate, sorbitan monostearate, sorbitan distearate, sorbitan tristearate, sorbitan monooleate, sorbitan trioleate, and sorbitan sesquioleate; examples of polyoxyethylene sorbitan fatty acid ester encompass polyoxyethylene sorbitan monostearate; examples of glycerine fatty acid ester encompass glycerol monostearate and glycerol monooleate; and examples of sucrose fatty acid ester encompass sucrose stearate, sucrose palmitate, sucrose oleate, sucrose laurate, and sucrose erucic acid ester.

According to the surfactant whose HLB is 10 or less or a surfactant whose HLB is greater than 10 described below, an n-number (i.e., the number of moles) of polyoxyethylene thereof is determined as appropriate in order to adjust HLB and the like. The polyoxyethylene can be monomolecular (i.e., identical n-number) or can be a mixture (i.e., average n-number/average added number of moles), and is selected from a range of 2 to 200, further from a range of 4 to 100, and preferably from a range of 8 to 80. If needed, it is possible to also use, in combination, 0 mol % to 30 mol %, further a small amount, i.e., approximately 0 mol % to 10 mol % of a polyoxypropylene unit.

As the surfactant whose HLB is 10 or less, it is possible to use RHEODOL series manufactured by Kao Corporation. Examples of the RHEODOL series encompass RHEODOL AO-15V, RHEODOL MS-60, RHEODOL MO-60A-15V, and the like whose HLB is in a range of 0 to 10 (catalog value).

The surfactant whose HLB is 10 or less is preferably polyoxyethylene stearyl ether (manufactured by Kao Corporation, EMULGEN 306P: HLB 9.4 (catalog value)), sorbitan fatty acid ester (manufactured by Kao Corporation, RHEODOL AO-15V: HLB 3.7 (catalog value)), glycerine fatty acid ester (manufactured by Kao Corporation, EXCEL series and RHEODOL series: HLB 2.8 to 3.8 (catalog value)), and particularly preferably glycerine fatty acid ester.

(Dispersion Liquid of Surfactant Whose HLB is 10 or Less)

The surfactant whose HLB is 10 or less is preferably added as a dispersion liquid (emulsion).

In order to uniformly add the surfactant whose HLB is 10 or less, an amount of water which is added together with the surfactant whose HLB is 10 or less is preferably 0.5 part by mass to 3.0 parts by mass, more preferably 0.7 part by mass to 2.0 parts by mass, still more preferably 0.8 part by mass to 2.0 parts by mass, relative to 100 parts by mass of water absorbent resin particles to be added. In a case where the amount of water is 0.5 part by mass or less, it may be difficult to uniformly add the surfactant whose HLB is 10 or less and damage resistance can unfavorably decrease. In a case where the amount of water is more than 3.0 parts by mass, a fluidity of water absorbent resin particles, which have absorbed water, decreases, and therefore it may be difficult to uniformly add the surfactant whose HLB is 10 or less due to insufficient stirring and mixing. Further, surprisingly, a bulk specific gravity unfavorably decreases and therefore the effect of the present invention cannot be brought about.

In the dispersion liquid of the surfactant whose HLB is 10 or less, the surfactant whose HLB is 10 or less is preferably uniformly dispersed in the liquid at a time point of the surfactant adding step of adding the surfactant whose HLB is 10 or less. Here, the term "dispersion" indicates a state of being semitransparently dissolved, preferably in a state of emulsion (i.e., a state of being emulsified). A dispersion element can be large to an extent of being viewed by eyes.

A transparent uniform solution and an unstable dispersion liquid, which causes phase separation in shorter than one minute after a dispersion liquid is prepared, are not preferable because the effect of the present invention may not be sufficiently brought about.

Note that the dispersion liquid is preferably used in the surfactant adding step soon after the dispersion liquid is prepared, in order to add the dispersion liquid in a uniform state. Specifically, the dispersion liquid is preferably added to the water absorbent resin particles before two days (i.e., 48 hours) elapse, more preferably before 1 day (i.e., 24 hours) elapses, from when the dispersion liquid is prepared.

A dispersion particle diameter of the surfactant whose HLB is 10 or less in the dispersion liquid is not limited to a particular one. However, in a case where the dispersion particle diameter is excessively large, the effect of the present invention may not be sufficiently brought about because stability of the dispersion liquid decreases and phase separation occurs in the dispersion liquid.

Therefore, as the dispersion liquid of the surfactant whose HLB is 10 or less, it is preferable to use a dispersion liquid that satisfies conditions of at least one of a dispersion liquid 1 and a dispersion liquid 2 below.

(Dispersion Liquid 1)

It is preferable to stir a dispersion liquid for 1 minute or more under conditions in which (i) a temperature of the dispersion liquid is at 40° C. to 100° C., more preferably 60° C. to 100° C., and still more preferably 70° C. to 100° C. and (ii) a rotating speed is at 1000 rpm or higher or a blade tip peripheral velocity of a stirring member/impeller is at 2.5 m/s or higher. Note that the blade tip peripheral velocity is more preferably 3.0 m/s or higher, still more preferably 3.5 m/s or higher, preferably 30 m/s or lower, more preferably 20 m/s or lower, and particularly preferably 10 m/s or lower. In a case where the blade tip peripheral velocity is excessively high, a stirring effect corresponding (i.e., proportional) to the blade tip peripheral velocity cannot be brought about and an unnecessary trouble such as breakage of the impeller may be caused. Therefore, it is preferable to avoid excessively high blade tip peripheral velocity.

(Dispersion Liquid 2)

It is possible to use a dispersion liquid in which dispersibility of the surfactant whose HLB is 10 or less is enhanced by using a water-soluble dispersing agent. A used amount of the water-soluble dispersing agent is preferably 0.1 to 9.0 times, more preferably 1.0 to 9.0 times as large, by mass, as that of the surfactant whose HLB is 10 or less.

(Water-Soluble Dispersing Agent)

The term "water-soluble" indicates a compound which is dissolved by 1 g or more, preferably 10 g or more, relative to 100 g of water (at 25° C.).

The water-soluble dispersing agent can be a nonionic surfactant whose HLB is greater than 10, an anionic surfactant, a cationic surfactant, an amphoteric surfactant, a water-soluble polymer, or a hydrophilic organic solvent (lower monohydric or polyhydric alcohol). Note that the HLB is preferably 13 or more. The n-number of polyoxyethylene in each of the following surfactant is preferably selected as appropriate within the above described range, as with the surfactant whose HLB is 10 or less.

Specifically, examples of the nonionic surfactant whose HLB is greater than 10 encompass polyoxyethylene alkyl ethers such as polyoxyethylene lauryl ether, polyoxyethylene cetyl ether, polyoxyethylene stearyl ether, polyoxyethylene oleyl ether, polyoxyethylene alkyl ether, polyoxyethylene myristyl ether, and polyoxyethylene octyldodecyl ether; a polyoxyalkylene derivative such as polyoxyethylene alkylene alkyl ether; polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, and polyoxyethylene sorbitan triisostearate; polyoxyethylene sorbitol fatty acid ester such as tetraoleic acid polyoxyethylene sorbitol; polyoxyethylene fatty acid esters such as polyethylene glycol monolaurate, polyoxyethylene glycol monostearate, and polyethylene glycol distearate; sucrose fatty acid esters such as sucrose stearate, sucrose palmitate, sucrose myristate, sucrose oleate, sucrose laurate, and polyoxyethylene hydrogenated castor oil; and the like.

Examples of the anionic surfactant encompass alkyl sulfate ester salts such as sodium lauryl sulfate, higher alcohol sodium sulfate, triethanolamine lauryl sulfate, and ammonium lauryl sulfate; sulfate salt of polyoxyethylene alkyl ether such as polyoxyethylene lauryl ether sodium sulfate, polyoxyethylene alkyl ether sodium sulfate, and triethanolamine sulfate salt of polyoxyethylene alkyl ether; sulfonates such as dodecylbenzenesulfonate, sodium alkyl-naphthalenesulfonate, sodium dialkyl sulphosuccinate, sodium alkyl diphenyl ether disulfonate, and sodium alkane sulfonate; fatty acid salts such as stearic acid soda soap, oleic acid potash soap, and castor oil potash soap; naphthalenesulfonic acid formalin condensates such as sodium salt of β-naphthalenesulfonic acid formalin condensate and sodium salt of special aromatic sulphonic acid formalin condensate; and a polymer surfactant such as a special polycarboxylic acid polymer surfactant.

Examples of the cationic surfactant encompass alkylamine salts such as coconut amine acetate and stearylamine acetate; quaternary ammonium salts such as lauryltrimethylammonium chloride, stearyltrimethylammonium chloride, cetyltrimethylammonium chloride, distearyldimethylammonium chloride, and alkylbenzyldimethylammonium chloride; and the like.

Examples of the amphoteric surfactant encompass alkylbetaine, alkylamine oxide lauryl betaine, stearyl betaine, lauryldimethylamine oxide, and the like.

Examples of the water-soluble polymer encompass polycarboxylates such as polyacrylate, alginate, and sodium carboxymethylcellulose; polysulfonate such as alkylnaphthalenesulfonic acid formalin condensate; nonionic polymers such as polyvinyl alcohol, water-soluble starch, and polyglycerine fatty acid ester; and the like. In an acid-group-containing water-soluble polymer, monovalent salt or polyvalent salt, in particular, monovalent salt can be used.

Among those, a nonionic surfactant, an anionic surfactant, and alginic acid or salt therefore (particularly, sodium salt) are preferable, and a nonionic surfactant and monovalent salt of alginic acid (particularly, sodium salt) are more preferable. Example of RHEODOL series manufactured by Kao Corporation and used as the water-soluble dispersing agent used in the present invention encompasses RHEODOL TW-S120V whose HLB is greater than 10 (catalog value), etc.

(2-8) Drying Step after Addition

After the surfactant adding step of adding the surfactant whose HLB is 10 or less, a drying step (hereinafter, sometimes referred to as "drying step after addition") is preferably provided. This step is aimed at adjusting a moisture content of the water absorbent resin particles to fall within a range from 3.0 mass % to 6.0 mass %, and a drying method is not limited to a particular one provided that the moisture content can be adjusted to an intended value without damaging the water absorbent resin particles.

As a concrete condition, a drying temperature is preferably 250° C. or lower, more preferably 200° C. or lower, still more preferably 150° C. or lower, further still more preferably 100° C. or lower, and particularly preferably 80° C. or lower, and 0° C. or higher in order to avoid an unfavorable phenomenon such as freezing. Moreover, it is preferable to expose the water absorbent resin particles to gas such as air or nitrogen but forced draft operation is not necessarily needed. Note that the gas is not limited to a particular one, provided that the gas is inert gas that does not contain moisture vapor whose pressure is equal to or higher than saturated vapor pressure.

For example, a method can be employed in which, after the surfactant adding step of adding the surfactant whose HLB is 10 or less, the water absorbent resin particles are placed in a dryer in a still state at a temperature of approximately 40° C. to 70° C. for 10 minutes to 60 minutes. Alternatively, for example, a method can be employed in which the water absorbent resin particles are exposed to atmospheric air at a room temperature for several hours, and the like.

(2-9) Additive Adding Step of Adding Other Additive

An additive adding step of adding other additives includes a water-insoluble fine particles adding step, a chelating agent adding step, a deodorant component adding step, and the like. These additives can be added depending on purposes. In a case where the other additives are added, such other additives need to be added before the surfactant adding step of adding the surfactant whose HLB is 10 or less.

(i) Water-Insoluble Fine Particles Adding Step

The water-insoluble fine particles used in this step are not limited in particular, provided that, when the water absorbing agent comes in contact with an aqueous liquid, the water-insoluble fine particles inhibit particles of the water absorbing agent from cohering with one another so that the aqueous liquid flows well. Among these, water-insoluble inorganic fine powder is preferable, and inorganic fine particles such as bentonite, silicon dioxide, titanium oxide, aluminum oxide, silicon fine particles are preferable.

The water-insoluble fine particles have a volume average particle diameter of preferably 10 μm or smaller, more preferably 5 μm or smaller, still more preferably 1 μm or smaller, and particularly preferably 0.5 μm or smaller.

The water absorbent resin and the water-insoluble fine particles can be mixed by dry blending or the water absorbent resin can be mixed with use of a slurry (i.e., a dispersion liquid) of the water-insoluble fine particles. It is preferable to employ the dry blending, and a mixer used in the dry blending is selected as appropriate.

A ratio of the water-insoluble fine particles relative to 100 parts by mass of the water absorbent resin is preferably 0.4 part by mass or less, more preferably 0.3 part by mass or less, still more preferably 0.2 part by mass or less, and particularly preferably 0.1 part by mass or less. A lower limit is preferably 0.001 part by mass or more, and more preferably 0.01 part by mass or more.

In a case where a content of the water-insoluble fine particles relative to 100 parts by mass of the water absorbent resin in the particulate water absorbing agent is more than 0.4 part by mass, AAP may significantly decrease by mixing.

(ii) Chelating Agent Adding Step

The particulate water absorbing agent of the present invention can further contain a chelating agent. By thus containing the chelating agent, the particulate water absorbing agent can have an excellent urine resistance and color protection.

This step can be carried out in an arbitrary order, and is preferably carried out before the surfactant adding step of adding the surfactant whose HLB is 10 or less. The chelating agent adding step can be carried out simultaneously with any of the above described steps, and is preferably carried out simultaneously with at least one of the polymerization step, the surface crosslinking step, and a granulating step below, and the chelating agent is more preferably added to the monomer or the monomer solution in the polymerization step.

A form of addition of the chelating agent is not limited to a particular one. For example, the chelating agent can be added in a liquid form or a solid (powder) form as it is, or can be added as a solution that is obtained by dissolving the chelating agent in a solvent in advance. From the viewpoint of handleability, variation in added amount, and the like, it is preferable to add the chelating agent in the solution form.

The chelating agent is preferably a polymer chelating agent and/or a non-polymer chelating agent, and more preferably a non-polymer chelating agent, and a molecular weight or a mass average molecular weight is preferably 40 to 2000, more preferably 60 to 1000, and still more preferably 100 to 500.

Specifically, the chelating agent can be aminocarboxylic acid (salt), and the number of carboxyl groups thereof is preferably 2 to 20, more preferably 4 to 10, and particularly preferably 5 to 8.

In the present invention, a used amount of the chelating agent is preferably 0.00001 part by mass to 10 parts by mass, more preferably 0.0001 part by mass to 1 part by mass, and still more preferably 0.002 part by mass to 0.1 part by mass, relative to 100 parts by mass of the water absorbent resin.

In a case where the chelating agent content relative to 100 parts by mass of the water absorbent resin in the particulate water absorbing agent is more than 10 parts by mass, there occur problems, for example, that an effect that matches the content cannot be brought about (i.e., uneconomical) and an absorption performance deteriorates. On the other hand, in a case where the content is less than 0.00001 part by mass, a sufficient effect of addition of the chelating agent cannot be brought about.

(iii) Deodorant Component Adding Step

It is possible to obtain a particulate water absorbing agent that is excellent in deodorizing property, by adding a deodorant component, preferably a plant component to the particulate water absorbing agent for the purpose of adding a deodorizing property. The deodorant component adding step of adding the deodorant component can be carried out as an optional step provided that the step is carried out before the surfactant adding step of adding the surfactant whose HLB is 10 or less, and is more preferably carried out after the surface crosslinking step.

The plant component is not limited to a particular one, and examples of the plant component encompass a compound that contains polyphenol, flavone, caffeine, tannin, tannic acid, nutgall, gallnut, gallic acid, or the like; Theaceae plants such as *Camellia*, *Eurya*, and *Ternstroemia*; Gramineae plants such as rice, bamboo grass, bamboo, corn, and barley, wheat and oat; Rubiaceae plants such as coffee; and the like. A form of the plant components is not limited to a particular one and can be, for example, an extract (essential oil) extracted from a plant, a plant itself, and plant residue and extract residue which are by-products generated in a production process in plant-processing industry and in food-processing industry.

A used amount of the plant component in the present invention is 0 part by mass to 10 parts by mass, preferably 0.001 part by mass to 5 parts by mass, and still more preferably 0.002 part by mass to 3 parts by mass, relative to 100 parts by mass of the water absorbent resin. The used amount within the above described range makes it possible to achieve the deodorizing property.

(2-10) Granulating Step and Fine Powder Recycling Step

In the present invention, the water absorbent resin can be granulated. In such a case, the granulating step needs to be carried out before the surfactant adding step of adding the surfactant whose HLB is 10 or less. In the granulating step, a hydrophilic organic solvent can be used in addition to water. Moreover, a fine powder recycling step can be carried out so that fine powder after classification is recycled in steps before the classification step, preferably in the polymerization step, the gel-crushing step, and the drying step.

(2-11) Fine Powder Recycling Step

After the drying step, it is preferable to carry out a classification step (including a second classification step after the surface crosslinking step; the same applies to descriptions below) in which water absorbent resin fine particles that have passed through a standard sieve having a mesh size of 150 μm are separated so that the water absorbent resin fine particles and a water additive thereof are recycled (i.e., reused) in steps before the drying step. Note that coarse particles removed in the classification step can be re-pulverized if needed. Moreover, fine particles removed in the classification step can be discarded, used for another purpose, or used in this fine powder recycling step.

By removing the fine particles, it is possible to improve liquid permeability (e.g., SFC). Moreover, by this step, it is possible to further improve a water absorbing speed (e.g., FSR).

That is, according to the producing method of the present invention, the fine powder recycling step indicates a step in which (i) water absorbent resin fine particles (in particular, including particles having a particle diameter of 150 μm or smaller by 70 mass % or higher; hereinafter, also referred to as "fine powder"), which are generated in the drying step and, if needed, the pulverizing step and the classification step, are separated and then (ii) the water absorbent resin fine particles as they are or hydrated or granulated are recycled before the drying step, preferably recycled in the polymerization step, the gel-crushing step, or the drying step.

By thus recycling the fine powder, the particle size of the water absorbent resin and the water absorbing agent can be controlled, and it is also possible to further improve the water absorbing speed by this step.

The fine powder to be recycled can be fine powder before or after the surface crosslinking, and an amount of recycling the fine powder is preferably 1 mass % to 40 mass % of a dried polymer, and more preferably 5 mass % to 30 mass % of the dried polymer.

A preferable method for recycling fine powder in the present invention is a method in which water absorbent resin fine powder or a hydrate or a granulated substance thereof, and if needed inorganic fine particles, and the like are mixed with a monomer aqueous solution before polymerization or with a hydrogel during polymerization. Examples of the method for recycling the fine powder so as to add the fine powder to the monomer aqueous solution before polymerization are disclosed in International Publications No. 92/001008 and No. 92/020723. Examples of the method for recycling the fine powder so as to add the fine powder to the hydrogel during polymerization are disclosed in International Publications No. 2007/074167, No. 2009/109563, No. 2009/153196, and No. 2010/006937. Moreover, examples of the method for recycling to the drying step (dryer) are disclosed in U.S. Pat. No. 6,228,930 and the like. Any of these methods for recycling fine powder is preferably employed.

[3] Physical Properties of Particulate Water Absorbing Agent

The present invention provides, as an example, (I) the above described method for producing a particulate water absorbing agent and (II) the novel particulate water absorbing agent which (i) contains the polyacrylic acid (salt)-based water absorbent resin as a main component and (ii) achieves physical properties described below. Note that respective methods for measuring the physical properties are described in Examples below.

The water absorbing agent (first water absorbing agent) of the present invention contains a polyacrylic acid (salt)-based water absorbent resin as a main component, has a Hausner ratio of less than 1.18, and has a water absorbing speed (FSR) of 0.25 [g/g/s] or higher.

The water absorbing agent (second water absorbing agent) of the present invention contains a polyacrylic acid (salt)-based water absorbent resin as a main component, has a moisture content of 3.0 mass % to 6.0 mass % or further contains a liquid permeability improving agent, and contains a surfactant whose HLB is 10 or less by 30 parts by weight to 150 parts by weight relative to 1000000 parts by weight of a water absorbent resin solid content.

The first water absorbing agent and the second water absorbing agent can be identical water absorbing agents (i.e., water absorbing agent that concurrently satisfies both the characteristics) or can be different water absorbing agents (i.e., water absorbing agent that satisfies only one of the characteristics). Each of the first water absorbing agent and the second water absorbing agent is preferably the water absorbing agent that concurrently satisfies both the characteristics.

The water absorbing agent of the present invention preferably has a bulk specific gravity of 0.61 g/ml or more and 0.80 g/ml or less, more preferably has a bulk specific gravity falling within a range described later. The water absorbing agent of the present invention preferably contains a liquid permeability improving agent. The water absorbing agent of the present invention preferably has particles of smaller than 150 μm after impact resistance test at a particle ratio of 0 mass % to 4.6 mass %.

Further, the first water absorbing agent and the second water absorbing agent preferably satisfy the following physical properties.

(3-1) Water Absorption Capacity Under Load (AAP)

In order to prevent leakage from a disposable diaper by, for example, the surface crosslinking after polymerization, a water absorption capacity (AAP) of the particulate water absorbing agent relative to a 0.9 wt % of sodium chloride aqueous solution is controlled under a pressure of 1.9 kPa or of 4.8 kPa to preferably 20 [g/g] or higher, more preferably 22 [g/g] or higher, and still more preferably 24 [g/g] or higher. An upper limit of the AAP is preferably as high as possible. However, from the viewpoint of a balance with the other physical properties, the upper limit of AAP is, generally, preferably 40 [g/g] and further preferably 35 [g/g]. In particular, in a case where the load is 4.8 kPa, the AAP is preferably approximately 30 [g/g].

(3-2) Water Absorption Capacity without Load (CRC)

A water absorption capacity without load (CRC) of the particulate water absorbing agent of the present invention is controlled to preferably 10 [g/g] or higher, more preferably 20 [g/g] or higher, still more preferably 25 [g/g] or higher, and particularly preferably 30 [g/g] or higher. Note that an upper limit of the water absorption capacity without load (CRC) is preferably as high as possible. However, from the viewpoint of a balance with the other physical properties (in particular, liquid permeability), the water absorption capacity without load (CRC) is preferably 50 [g/g] or lower, more preferably 45 [g/g] or lower, and still more preferably 40 [g/g] or lower. The CRC can be controlled by adjusting an amount of a crosslinking agent and the like.

(3-3) SFC (Saline Flow Conductivity)

In order to prevent leakage from a disposable diaper by, for example, the polymerization and the surface crosslinking carried out while the particle size is controlled, a saline flow conductivity relative to 0.69 wt % of saline (SFC), which is a liquid permeability under load, of the particulate water absorbing agent is controlled to 1 $[\times 10^{-7} \cdot cm^3 \cdot sec \cdot g^{-1}]$ or more, preferably 20 $[\times 10^{-7} \cdot cm^3 \cdot sec \cdot g^{-1}]$ or more, 50 $[\times 10^{-7} \cdot cm^3 \cdot sec \cdot g^{-1}]$ or more, 70 $[\times 10^{-7} \cdot cm^3 \cdot sec \cdot g^{-1}]$ or more, in this order, and particularly 100 $[\times 10^{-7} \cdot cm^3 \cdot sec \cdot g^{-1}]$ or more. An upper limit is determined as appropriate from the viewpoint of a balance with the other physical properties (in particular, CRC), and is generally 2000 $[\times 10^{-7} \cdot cm^3 \cdot sec \cdot g^{-1}]$ or less, 1000 $[\times 10^{-7} \cdot cm^3 \cdot sec \cdot g^{-1}]$ or less, and 500 $[\times 10^{-7} \cdot cm^3 \cdot sec \cdot g^{-1}]$ or less. Note that the SFC can be defined by a known measuring method, e.g., a method disclosed in U.S. Pat. No. 5,562,646.

(3-4) FSR (Water Absorbing Speed)

A water absorbing speed (FSR) of 1 g of the particulate water absorbing agent of the present invention relative to 20 g of a physiological saline solution is generally 0.05 [g/g/sec] or more, preferably 0.10 [g/g/sec] or more, more preferably 0.15 [g/g/sec] or more, still more preferably 0.20 [g/g/sec] or more, and particularly preferably 0.25 [g/g/sec] or more. An upper limit is preferably 0.50 [g/g/sec] or less. A method for measuring the FSR is defined by a method disclosed in the pamphlet of International Publication No. 2009/016055.

(3-5) Bulk Specific Gravity

A bulk specific gravity of the particulate water absorbing agent is generally 0.55 [g/ml] to 0.80 [g/ml], preferably 0.61 to 0.80 [g/ml], and still more preferably 0.65 [g/ml] to 0.75 [g/ml].

Moreover, in measuring a Hausner ratio (later described), a loose bulk density and a tight bulk density (i.e., bulk density after properly filling by vibration (tapping)) are measured, and a Hausner ratio is calculated based on a ratio of the tight bulk density to the loose bulk density.

The water absorbing agent of the present invention is characterized by having a low Hausner ratio and a high bulk specific gravity. When the Hausner ratio is low, it is difficult to carry out filling by vibration. That is, according to the producing method of the present invention, it is possible to densely fill with the water absorbing agent without applying vibration which may adversely influence properties. Furthermore, it is possible to obtain the excellent water absorbing agent whose properties are hardly influenced by vibration.

By the present invention, it is possible to improve both the FSR and the bulk specific gravity, which has been difficult to achieve by conventional techniques.

(3-6) Surface Tension

A surface tension (defined by a measuring method in Examples) of the particulate water absorbing agent in accordance with the present invention is preferably 55 [mN/m] or more, more preferably 60 [mN/m] or more, still more preferably 65 [mN/m] or more, particularly preferably 70 [mN/m] or more, and most preferably 72 [mN/m] or more. There is no substantial decrease in surface tension. A sufficient upper limit is generally 75 [mN/m].

(3-7) Moisture Content

A moisture content of the particulate water absorbing agent in accordance with the present invention is preferably 3.0 parts by weight or more and 6.0 parts by weight or less, more preferably 3.0 parts by weight or more and 5.5 parts by weight or less, and most preferably 3.5 parts by weight or more and 5.0 parts by weight or less. In a case where the moisture content is less than 3.0 parts by weight, there is a problem that damage resistance decreases. In a case where the moisture content is more than 6.0 parts by weight, a bulk specific gravity unfavorably decreases.

(3-6) Other Physical Properties

The form of the particulate water absorbing agent according to the present invention is not limited to a particular one, provided that the particulate water absorbing agent has a particle form. The particulate water absorbing agent may have, for example, a spherical form, a substantially spherical form, an irregularly crushed piece form (that is, a crushed substance), a bar form, a polygonal form, a sausage form (for example, U.S. Pat. No. 4,973,632 etc.), a wrinkled particle form (for example, U.S. Pat. No. 5,744,564 etc.), or the like. Such particles can be primary particles (single particles), granulated particles, or a mixture thereof. Further, these particles can be expanded porous particles. Among these particles, irregularly crushed primary particles or granulated particles are preferable.

The mass average particle diameter (D50) of the particulate water absorbing agent is preferably 200 μm to 600 μm, more preferably 250 μm to 550 μm, and still more preferably 350 μm to 500 μm.

Further, the logarithmic standard deviation (σζ) of the particle size distribution is preferably 0.20 to 0.50, more preferably 0.25 to 0.45, and still more preferably 0.30 to 0.35.

Further, according to the particulate water absorbing agent of the present invention, a smaller ratio of coarse particles having a particle diameter of 850 μm or more (defined by JIS standard sieve) is more preferable. A ratio of such coarse particles is 0 mass % to 5 mass % in general, preferably 0 mass % to 3 mass %, and more preferably 0 mass % to 1 mass %.

Furthermore, according to the particulate water absorbing agent of the present invention, a smaller ratio of fine particles having a particle diameter of less than 150 μm (defined by JIS standard sieve) is more preferable. A ratio of such fine particles is 0 mass % to 5 mass % in general, preferably 0 mass % to 3 mass %, and more preferably 0 mass % to 1 mass %.

The above-described particle size (mass average particle diameter (D50), logarithmic standard deviation (σζ), ratio of coarse particles or fine particles) and the bulk specific gravity are suitably applied not only to the water absorbent resin particle but also to a surface-crosslinked water absorbent resin and an ultimate particulate water absorbing agent. In a case where the particle size is out of the above-described range, decrease in water absorption capacity under load (AAP) and increase in returned liquid amount (Re-Wet) in a disposable diaper are observed. Therefore, such a particle size is not preferable.

[4] Application Etc. of Particulate Water Absorbing Agent

Applications of the particulate water absorbing agent according to the present invention are not limited in particular. However, the particulate water absorbing agent is preferably formed into an absorbent body and then used for absorbent articles (for example, disposable diapers) as ultimate consumable goods.

(4-1) Absorbent Body

The absorbent body in the present invention is obtained by forming the particulate water absorbing agent into a sheet form, a web form, a cylindrical form, or the like. Note that the "absorbent body" means a water-absorbing material obtained by forming, into a shape, the particulate water absorbing agent and a hydrophilic fiber such as pulp as main components.

Further, the particulate water absorbing agent of the present invention has an excellent liquid permeability (SFC). Therefore, in a case where the particle water absorbing agent is used for the absorbent body, a content of the hydrophilic fiber can be reduced. Accordingly, even when a core concentration is arranged to be 40 mass % or higher, an excellent liquid diffusion property is obtained. This makes it possible to quickly absorb and diffuse a large amount of aqueous liquid at once. Furthermore, the absorption performance can be maintained for a long time, and additionally, there occurs no return of absorbed aqueous liquid. As described above, use of the particulate water absorbing agent of the present invention makes it possible to actually reduce a thickness of the absorbent body (particularly, a disposable diaper).

(4-2) Absorbent Article

The absorbent article in the present invention is ultimate consumable goods that are intended for water absorption, gelatification, moisture retention, waterproof, moisture absorption, and the like. The ultimate consumable goods are absorbent articles including the absorbent body, a front surface sheet having liquid permeability, and a liquid-impermeable back surface sheet. Specifically, examples of the absorbent particles encompass a disposable diaper, an incontinence pad, a sanitary napkin, etc., and particularly preferably a disposable diaper. Note that the absorbent article can also be applied to other hygiene materials.

EXAMPLES

[5] Examples

The following description will further discuss the present invention with reference to Examples. Note, however, that the present invention should not be interpreted as being limited to Examples. Moreover, the physical properties in claims and Examples of the present invention were obtained in accordance with the following measuring methods (5-1) through (5-9). Note that, unless otherwise noted, steps in Examples were carried out substantially at a normal pressure (i.e., within ±5% and still more preferably within 1% relative to an atmospheric pressure). Further, the same step was carried out without changing the pressure, i.e., without intentionally heightening or lowering the pressure.

(5-1) Weight Average Particle Diameter (D50) and Logarithmic Standard Deviation (σζ) of Particle Size Distribution A weight average particle diameter (D50) (unit; [μm]) and a logarithmic standard deviation (σζ) of particle size distribution were obtained by classification carried out with the use of a standard sieve in conformity with US Patent Application Publication No. 2006-204755.

(5-2) CRC (Water Absorption Capacity without Load)

In conformity with ERT441.2-0.2, a water absorption capacity (CRC) (unit; [g/g]) relative to a 0.90 wt % of sodium chloride aqueous solution (also referred to as "physiological saline solution") for 30 minutes without load was obtained.

(5-3) Solid Content and Moisture Content

A solid content is a ratio of a component, which is not volatilized at 180° C., in the particulate water absorbing agent. The following indicates a relation between a solid content and a moisture content:

Solid content [wt %]=100−moisture content [wt %]

The solid content was measured with the following method.

Approximately 1 g of the particulate water absorbing agent (weight of W2 [g]) was put in an aluminum cup (weight of W1 [g]) having a bottom surface diameter of approximately 5 cm, and then dried by being placed in a windless dryer at 180° for 3 hours in a still state. A total weight (W3 [g]) of the aluminum cup and the particulate water absorbing agent after the drying was measured, and a solid content was calculated based on (Math. 1).

Solid content [wt %]={(W3−W1)/W2}×100    (Math. 1)

(5-4) FSR (Water Absorbing Speed)

1.00 g of the particulate water absorbing agent was put in a 25 ml glass beaker (having a diameter of 32 mm to 34 mm and a height of 50 mm). In this case, an upper surface of the particulate water absorbing agent in the beaker was made to level (if needed, the surface of the particulate water absorbing agent may be made to level by, for example, carefully tapping the beaker).

Next, 20 g of a 0.90 wt % of sodium chloride aqueous solution whose temperature had been adjusted to 23° C.±0.2° C. was put in a 50 ml glass beaker, and a total weight (weight of W4 [g]) of the sodium chloride aqueous solution and the glass beaker was measured. The sodium chloride aqueous solution thus weighed was poured carefully and quickly into the 25 ml beaker containing the particulate water absorbing agent. At a timing at which the poured sodium chloride aqueous solution made contact with the particulate water absorbing agent, time measurement was started. Then, the time measurement was ended (time is [second]) at a time point at which an upper surface, which was first a surface of the sodium chloride aqueous solution poured into the beaker, was replaced with a surface of the particulate water absorbing agent which was absorbed the sodium chloride aqueous solution when the upper surface was viewed by eyes at an angle of approximately 20°.

Next, a weight (weight of W5 [g]) of the 50 ml glass beaker which had been emptied of the sodium chloride aqueous solution was measured. A weight (weight of W6 [g]) of the poured sodium chloride aqueous solution was calculated based on (Math. 2), and a FSR (unit; [g/g/s]) was obtained based on (Math. 3).

W6[g]=W4−W5    (Math. 2)

FSR [g/g/s]=W6/(ts×weight [g] of particulate water absorbing agent)    (Math. 3)

(5-5) Bulk Specific Gravity

A bulk specific gravity was measured with the use of a bulk specific gravity measuring device (manufactured by Kuramochi Scientific Instrument Seisakusho) in conformity with JIS K 3362. After 50.0 g of a particulate water absorbing agent, which was sufficiently stirred so as to prevent deviation due to difference in particle size, was put in a funnel with a closed damper, the damper was opened quickly so that the particulate water absorbing agent was poured into 42 ml glass receiver (having an inner diameter of 32 mm, an outer diameter of 35 mm, a height of 52 mm, and a weight of W7 [g]). A part of the particulate water absorbing agent, which part was protruding on the receiver, was removed with the use of a glass rod such that an upper surface is leveled off from a measurer side to an opposite side. After that, a weight (weight of W8 [g]) of the receiver containing the particulate water absorbing agent was accurately measured to the unit of ¹/₁₀ g, and a bulk specific gravity (unit; [g/ml]) was calculated based on (Math. 4).

$$\text{Bulk specific gravity [g/ml]}=(W8-W7)/42 \qquad \text{(Math. 4)}$$

Note that the measurement was carried out at an ambient temperature of 23.2° C. and at a relative humidity of 38% RH.

(5-6) Surface Tension 50 ml of a physiological saline solution, whose temperature had been adjusted to 23° C.±2° C., was put in 100 ml beaker which had been sufficiently washed. Then, a surface tension of the physiological saline solution was measured with the use of a surface tension meter (manufactured by KRUSS, K11 automatic surface tension meter). In this measurement, the surface tension needs to fall within a range from 71 [mN/m] to 75 [mN/m].

Next, (i) a rotor, which had been sufficiently washed, had a length of 25 mm, and had been coated with a fluorocarbon resin, and (ii) 0.5 g of a particulate water absorbing agent were put in the beaker containing the physiological saline solution whose (i) temperature had been adjusted to 23° C.±2° C. and (ii) surface tension had been measured, and then stirred at a rotating speed of 500 rpm for 4 minutes. After 4 minutes elapsed, the stirring was stopped, and then, after the particulate water absorbing agent absorbed water and was precipitated, a surface tension (unit; [mN/m]) of a supernatant liquid was measured with similar procedures. Note that, in the present invention, a plate method using a platinum plate was employed, and the plate was sufficiently washed with deionized water and also washed with heat by the use of a gas burner before being used in each of the measurements.

(5-7) Liquid Permeability (SFC)

SFC (unit; $[\times 10^{-7} \cdot cm^3 \cdot sec \cdot g^{-1}]$) was measured with a known measuring method disclosed in U.S. Pat. No. 5,562,646.

(5-8) Damage Resistance Test

By a method (of mechanical damage test) disclosed in Patent Literature 38 (U.S. Pat. No. 6,562,879) and in the corresponding Japanese Patent Application Publication "Tokukai No. 2000-302876" (page 12, paragraphs [0001] and [0002]), damage was applied to the particulate water absorbing agent. Then, 10 g of the particulate water absorbing agent, to which the damage had been applied, was classified with the use of a JIS standard sieve (JIS Z 8801-1 (2000)) having a mesh size of 150 μm or with the use of a sieve equivalent to the JIS standard sieve. After the classification, a particle content [wt %] of particles smaller than 150 μm was obtained with the use of a particle weight of particles having a particle size of smaller than 150 μm based on (Math. 5).

Particle content [wt %] of particles having particle size of smaller than 150 μm={(particle weight [g] of particles having particle size of smaller than 150 μm)/(weight [g] of particulate water absorbing agent)}×100 (Math. 5)

(5-9) Hausner Ratio

With the use of a method below, a Hausner ratio was calculated from a loose bulk density and a tight bulk density.

(Loose Bulk Density)

A loose bulk density was measured with the use of a powder tester (manufactured by HOSOKAWA MICRON CORPORATION, product name; Powder Tester PT-X). 40 g of a particulate water absorbing agent, which had been well stirred, was put in a 250 ml polypropylene container. A 25 cc measuring cup (weight of W9 [g]), which was supplied with the powder tester and whose weight was accurately measured to the unit of ¹/₁₀₀ g, was attached to the powder tester body, a lower part of shoot was sealed with a polypropylene sheet, and a sample was poured into a damper at an upper part of the measuring device. The polypropylene sheet was horizontally removed quickly so that the measuring cup is completely filled with the sample and further the sample overflows from the measuring cup. A part of the particulate water absorbing agent, which part was protruding from the measuring cup, was removed to level off with the use of a metal blade supplied with the powder tester, and after that, a weight (weight of W10 [g]) of the measuring cup containing the particulate water absorbing agent was accurately measured to the unit of ¹/₁₀₀ g, and a loose bulk density (unit; [g/ml]) was calculated based on (Math. 6).

$$\text{Loose bulk density [g/ml]}=(W10-W9)/25 \qquad \text{(Math. 6)}$$

(Tight Bulk Density)

A tight bulk density was measured with the use of the powder tester. 40 g of a particulate water absorbing agent, which had been well stirred, was put in a 250 ml polypropylene container. A cap (having an inner diameter identical with that of the measuring cup) supplied with the powder tester was attached to the 25 cc measuring cup (weight of W11 [g]), which was supplied with the powder tester and whose weight was accurately measured to the unit of ¹/₁₀₀ g, and the measuring cup was then attached to the powder tester body. The lower part of shoot was sealed with a polypropylene sheet, and a sample was poured into the damper at the upper part of the measuring device. The polypropylene sheet was horizontally removed quickly so that the measuring cup is completely filled with the sample and further the sample overflows from the measuring cup. The number of tapping was set to 180, and tapping was started. Each stroke of the tapping was fixed to 18 mm. After the tapping was finished, the cap was detached, and a part of the particulate water absorbing agent, which part was protruding from the measuring cup, was removed to level off with the use of the metal blade supplied with the powder tester. After that, a weight (weight of W12 [g]) of the measuring cup containing the particulate water absorbing agent was accurately measured to the unit of ¹/₁₀₀ g, and a tight bulk density (unit; [g/ml]) was calculated based on (Math. 7).

$$\text{Tight bulk density [g/ml]}=(W12-W11)/25 \qquad \text{(Math. 7)}$$

Note that the measurement was carried out at an ambient temperature of 23.5° C. and at a relative humidity of 38% RH.

(Hausner Ratio)

Based on (Math. 8), a Hausner ratio was calculated from the loose bulk density and the tight bulk density.

Hausner ratio [–]=tight bulk density [g/ml]/loose bulk density [g/ml] (Math. 8)

Production Example 1

In accordance with Example 23 of WO2011/078298, water absorbent resin particles were prepared.

595.4 [g/min] of a 37 wt % of sodium acrylate aqueous solution, 198.6 [g/min] of a 48 wt % of sodium hydroxide aqueous solution, 300.1 [g/min] of 100 wt % acrylic acid, 2.71 [g/min] of polyethylene glycol diacrylate (molecular weight of 523) as an internal crosslinking agent, 203.9 [g/min] of deionized water (ion-exchanged water), 0.42 [g/min] of a 31 wt % of diethylenetriamine pentaacetic acid-3 sodium aqueous solution, and 0.46 [g/min] of a 10 wt % of polyoxyethylene (20) sorbitan monostearate (manufactured by Kao Corporation) aqueous solution as a surfactant were continuously mixed with the use of a dispersing device, and 26.0 [g/min] of a 3 wt % of sodium persulfate aqueous solution was mixed by line mixing with a monomer aqueous solution which had passed through the dispersing device, and a mixture thus obtained was supplied to a belt polymerization device. The belt polymerization device included an endless belt which had a surface coated with a fluorocarbon resin and had a length of 3.8 m and a width of 60 cm. A temperature of a bottom surface side of the belt and a surrounding area of the polymerization device was heated up to and kept at approximately 90° C., and the belt polymerization device included a suction pipe which was provided at a center part of the belt polymerization device in order to recycle evaporative water. Moreover, a temperature of the monomer aqueous solution to be supplied onto the belt was controlled to 92° C. by supplying water to the dispersing device.

A temperature of a monomer aqueous solution (1) supplied to the polymerization device was 92° C., and an amount of dissolved oxygen was 4.30 [ml/L].

Note that, in this case, the monomer aqueous solution (1) containing the surfactant became whitish because extremely small gas bubbles were introduced due to decrease in gas solubility, and polymerization reaction started immediately after the monomer aqueous solution (1) was continuously supplied to the belt polymerization device. Then, polymerization was carried out in the polymerization device for approximately 2 minutes, and a belt-like hydrogel polymer (i.e., hydrogel) was continuously obtained from an outlet of the polymerization device. In the obtained gel, a water soluble component was 3.2 wt %, a solid content was 53 wt %, and a weight average molecular weight of the water soluble component was 229000 [Da].

Subsequently, the hydrogel thus obtained was cut by a length of 200 mm and crushed with the use of a screw extruder (meat chopper) having the following specifications. The screw extruder had a porous plate provided at an end part thereof, and a diameter of the porous plate was 100 mm, a pore diameter was 7.5 mm, the number of pores was 55, and a thickness of the porous plate was 6 mm. As gel-crushing conditions, a supplying rate of the hydrogel was set to 1600 [g/min], and hot water at 90° C. (supplying rate; 50 [g/min]) and moisture vapor (supplying rate; 70 [g/min]) were simultaneously supplied to the meat chopper, and a rotating speed of the screw shaft was 412 rpm. Note that a temperature of the hydrogel before gel-crushing was 94° C., and a temperature of the hydrogel after gel-crushing (hereinafter, referred to as "crushed gel") was 103° C.

With regard to a crushed gel (1) thus obtained, a weight average particle diameter (D50) was 897 μm, a logarithmic standard deviation (σζ) of particle size distribution was 0.98, a water soluble component was 3.8 wt %, and a solid content was 49.4 wt %.

Next, the crushed gel (1) thus obtained was spread over woven stainless-steel wires having a mesh size of 850 μm, and hot air drying was carried out at 180° C. for 30 minutes. Subsequently, a dried matter thus obtained by the drying operation was pulverized with the use of a roll mill (manufactured by Inoguchi Giken Ltd., WML-type roll crusher) and was then classified with the use of a JIS standard sieve having a mesh size of 850 μm and a JIS standard sieve having a mesh size of 45 μm. By the above operation, irregularly shaped pulverized form of base water absorbent resin particles (1) were obtained which had a solid content of 96 wt %, a weight average particle diameter (D50) of 445 μm, and a logarithmic standard deviation (σζ) of particle size distribution of 0.36.

A surface crosslinking agent, which was a mixed solution of 0.4 part by weight of ethylenecarbonate, 0.6 part by weight of propyleneglycol, 2.5 parts by weight of deionized water, and 0.001 part by weight of polyoxyethylene (20) sorbitan monostearate (manufactured by Kao Corporation) (10 ppm relative to water absorbent resin particles), was uniformly mixed with 100 parts by weight of the base water absorbent resin particles (1) thus obtained. After that, the mixture was surface-crosslinked by heating treatment at 180° C. for 45 minutes. After the heating treatment, the resultant water absorbent resin particles were crushed to a size with which the water absorbent resin particles passed through a JIS standard sieve having a mesh size of 850 μm, and thus the surface crosslinked water absorbent resin particles (1) were obtained.

Example 1

0.5 g of glycerine fatty acid ester (middle purity monoglyceride vegetable olein•stearin) (manufactured by Kao Corporation; product name: EXCEL 122V, HLB=3.5 (catalog value)), which served as a surfactant and had been dissolved at 60° C., and 49.5 g of deionized water (ion-exchanged water) at 75° C. were put in a cup supplied with a homogenizer (manufactured by NIHONSEIKI KAISHA Ltd.; MAXIM HOMOGENIZER MX-7), and were stirred at 5000 rpm for 5 minutes while being heated in a hot water bath at 75° C. Thus, a dispersion liquid (1) was prepared. The cup supplied with the homogenizer was a container which was made of stainless steel (SUS), had a bottom surface with an outer diameter of 71 mm, had an upper surface with an inner diameter of 112 mm, had a height of 130 mm, and had a capacity of approximately 850 ml. An impeller of the homogenizer included eight stirring blades each of which had a cutting edge on its one side. The eight stirring blades included four longer blades of 22 mm and four shorter blades of 18 mm, and each pair (i.e., 2) of the longer blades and each pair (i.e., 2) of the shorter blades were arranged alternately. Adjacent two of the longer blades were located on an upper side and a lower side, respectively.

Moreover, a mixed solution (1) was prepared which contained 0.91 part by weight of aluminum sulfate aqueous solution (8 wt % on aluminum oxide basis) as a polyvalent metal cation, 0.27 part by weight of a 60 wt % of sodium lactate aqueous solution, and 0.02 part by weight of propyleneglycol.

Next, 1.2 parts by weight of the mixed solution (1) was added, while being stirred, to 100 parts by weight of the surface crosslinked water absorbent resin particles (1) obtained in Production Example 1, and mixed for 1 minute, and then placed in a still state at a room temperature for 5 minutes. Subsequently, 1 part by weight (i.e., 100 ppm as the surfactant to the water absorbent resin) of the dispersion liquid (1) relative to 100 parts by weight of the surface crosslinked water absorbent resin particles (1) was added to the mixture, and uniformly mixed. Then, the mixture was dried at 60° C. for 30 minutes under a windless condition, and resultant particles were caused to pass through the JIS standard sieve having a mesh size of 850 μm. Thus, water absorbent resin particles (1) (also referred to as "water absorbing agent (1)") were obtained to which the dispersion liquid containing 100 ppm of the specific surfactant (EXCEL 122V) had been post-added. Preparation conditions of the water absorbent resin particles (1) thus obtained are indicated in Table 1, and physical properties of the water absorbent resin particles (1) are indicated in Tables 2 and 3.

Example 2

Operations similar to those of Example 1 were carried out except that (i) a used amount of glycerine fatty acid ester (middle purity monoglyceride vegetable olein•stearin) (manufactured by Kao Corporation; product name: EXCEL 122V) in preparation of a dispersion liquid was changed from 0.5 g to 0.25 g, (ii) a used amount of deionized water (ion-exchanged water) at 75° C. was changed from 49.5 g to 49.75 g, and (iii) an added amount of the dispersion liquid (1) was changed from 1 part by weight (i.e., 100 ppm as the surfactant to the water absorbent resin) relative to 100 parts by weight of the surface crosslinked water absorbent resin particles (1) to 2 parts by weight (i.e., 100 ppm as the surfactant to the water absorbent resin) relative to 100 parts by weight of the surface crosslinked water absorbent resin particles (1). Thus, water absorbent resin particles (2) (also referred to as "water absorbing agent (2)") were obtained to which the dispersion liquid containing 100 ppm of the specific surfactant (EXCEL 122V) had been post-added. Preparation conditions of the water absorbent resin particles (2) thus obtained are indicated in Table 1, and physical properties of the water absorbent resin particles (2) are indicated in Table 2.

Comparative Example 1

Operations similar to those of Example 1 were carried out except that the dispersion liquid (1) was not added, and comparative water absorbent resin particles (1) (also referred to as "comparative water absorbing agent (1)") were obtained. Preparation conditions of the comparative water absorbent resin particles (1) thus obtained are indicated in Table 1, and physical properties of the comparative water absorbent resin particles (1) are indicated in Tables 2 and 3.

Comparative Example 2

1 part by weight of deionized water (ion-exchanged water) was added, while being stirred, relative to 100 parts by weight of the comparative water absorbent resin particles (1) obtained in Comparative Example 1, and mixed for 1 minute. Subsequently, the mixture was put in a reclosable polyethylene bag (manufactured by SEISANNIPPONSHA Ltd.; product name: Uni-Pack D-4) and then the reclosable polyethylene bag was sealed and left at a room temperature for 2 days. Thus, comparative water absorbent resin particles (2) (also referred to as "comparative water absorbing agent (2)") were obtained. Preparation conditions of the comparative water absorbent resin particles (2) thus obtained are indicated in Table 1, and physical properties of the comparative water absorbent resin particles (2) are indicated in Table 2.

Comparative Example 3

Operations similar to those of Example 2 were carried out except that an added amount of the deionized water (ion-exchanged water) relative to 100 parts by weight of the comparative water absorbent resin particles (1) was changed from 1 part by weight to 5 parts by weight, and comparative water absorbent resin particles (3) (also referred to as "comparative water absorbing agent (3)") were thus obtained. Preparation conditions of the comparative water absorbent resin particles (3) thus obtained are indicated in Table 1, and physical properties of the comparative water absorbent resin particles (3) are indicated in Table 2.

Comparative Example 4

Operations similar to those of Example 1 were carried out except that (i) a used amount of glycerine fatty acid ester (middle purity monoglyceride vegetable olein•stearin) (manufactured by Kao Corporation; product name: EXCEL 122V) in preparation of a dispersion liquid was changed from 0.5 g to 0.125 g, (ii) a used amount of deionized water (ion-exchanged water) at 75° C. was changed from 49.5 g to 49.875 g, and (iii) an added amount of the dispersion liquid (1) was changed from 1 part by weight (i.e., 100 ppm as the surfactant to the water absorbent resin) relative to 100 parts by weight of the surface crosslinked water absorbent resin particles (1) to 4 parts by weight (i.e., 100 ppm as the surfactant to the water absorbent resin) relative to 100 parts by weight of the surface crosslinked water absorbent resin particles (1). Thus, comparative water absorbent resin particles (4) (also referred to as "comparative water absorbing agent (4)") were obtained to which the dispersion liquid containing 100 ppm of a specific surfactant (EXCEL 122V) had been post-added. Preparation conditions of the comparative water absorbent resin particles (4) thus obtained are indicated in Table 1, and physical properties of the comparative water absorbent resin particles (4) are indicated in Table 2.

Comparative Example 5

Operations similar to those of Example 1 were carried out except that (i) a used amount of glycerine fatty acid ester (middle purity monoglyceride vegetable olein•stearin) (manufactured by Kao Corporation; product name: EXCEL 122V) in preparation of a dispersion liquid was changed from 0.5 g to 0.05 g, (ii) a used amount of deionized water (ion-exchanged water) at 75° C. was changed from 49.5 g to 49.95 g, and (iii) an added amount of the dispersion liquid (1) was changed from 1 part by weight (i.e., 100 ppm as the surfactant to the water absorbent resin) relative to 100 parts by weight of the surface crosslinked water absorbent resin particles (1) to 10 parts by weight (i.e., 100 ppm as the surfactant to the water absorbent resin) relative to 100 parts by weight of the surface crosslinked water absorbent resin particles (1). Thus, comparative water absorbent resin particles (5) (also referred to as "comparative water absorbing agent (5)") were obtained to which the dispersion liquid containing 100 ppm of a specific surfactant (EXCEL 122V) had been post-added. Preparation conditions of the comparative water absorbent resin particles (5) thus obtained are indicated in Table 1, and physical properties of the comparative water absorbent resin particles (5) are indicated in Table 2.

Example 3

Operations similar to those of Example 1 were carried out except that a dispersion liquid (3) was used in which the glycerine fatty acid ester (middle purity monoglyceride vegetable olein•stearin) (manufactured by Kao Corporation; product name: EXCEL 122V) was replaced with the same weight of glycerine fatty acid ester (middle purity monoglyceride self-emulsifying stearin) (manufactured by Kao Corporation; product name: EXCEL P-40S, HLB=2.8 (catalog value)). Thus, water absorbent resin particles (3) (also referred to as "water absorbing agent (3)") were obtained to which the dispersion liquid containing 100 ppm of a specific surfactant (EXCEL P-40S) had been post-added. Preparation conditions of the water absorbent resin particles (3) thus obtained are indicated in Table 4, and physical properties of the water absorbent resin particles (3) are indicated in Tables 5 and 6.

Example 4

Operations similar to those of Example 1 were carried out except that a dispersion liquid (4) was used in which the glycerine fatty acid ester (middle purity monoglyceride vegetable olein•stearin) (manufactured by Kao Corporation; product name: EXCEL 122V) was replaced with the same weight of glycerine fatty acid ester (molecularly-distilled monoglyceride stearin) (manufactured by Kao Corporation; product name: EXCEL S-95, HLB=3.8 (catalog value)). Thus, water absorbent resin particles (4) (also referred to as "water absorbing agent (4)") were obtained to which the dispersion liquid containing 100 ppm of a specific surfactant (EXCEL S-95) had been post-added. Preparation conditions of the water absorbent resin particles (4) thus obtained are indicated in Table 4, and physical properties of the water absorbent resin particles (4) are indicated in Tables 5 and 6.

Example 5

Operations similar to those of Example 1 were carried out except that a dispersion liquid (5) was used in which the glycerine fatty acid ester (middle purity monoglyceride vegetable olein•stearin) (manufactured by Kao Corporation; product name: EXCEL 122V) was replaced with the same weight of glycerine fatty acid ester (glycerol monostearate) (manufactured by Kao Corporation; product name: RHEODOL MS-60, HLB=3.5 (catalog value)). Thus, water absorbent resin particles (5) (also referred to as "water absorbing agent (5)") were obtained to which the dispersion liquid containing 100 ppm of a specific surfactant (RHEODOL MS-60) had been post-added. Preparation conditions of the water absorbent resin particles (5) thus obtained are indicated in Table 4, and physical properties of the water absorbent resin particles (5) are indicated in Tables 5 and 6.

Example 6

Operations similar to those of Example 1 were carried out except that a dispersion liquid (6) was used in which the glycerine fatty acid ester (middle purity monoglyceride vegetable olein•stearin) (manufactured by Kao Corporation; product name: EXCEL 122V) was replaced with the same weight of glycerine fatty acid ester (glycerol monooleate) (manufactured by Kao Corporation; product name: RHEODOL MO-60, HLB=2.8 (catalog value)). Thus, water absorbent resin particles (6) (also referred to as "water absorbing agent (6)") were obtained to which the dispersion liquid containing 100 ppm of a specific surfactant (RHEODOL MO-60) had been post-added. Preparation conditions of the water absorbent resin particles (6) thus obtained are indicated in Table 4, and physical properties of the water absorbent resin particles (6) are indicated in Tables 5 and 6.

Example 7

Operations similar to those of Example 1 were carried out except that a dispersion liquid (7) was used in which the glycerine fatty acid ester (middle purity monoglyceride vegetable olein•stearin) (manufactured by Kao Corporation; product name: EXCEL 122V) was replaced with the same weight of sorbitan sesquioleate (manufactured by Kao Corporation; product name: RHEODOL AO-15V, HLB=3.7 (catalog value)). Thus, water absorbent resin particles (7) (also referred to as "water absorbing agent (7)") were obtained to which the dispersion liquid containing 100 ppm of a specific surfactant (RHEODOL AO-15V) had been post-added. Preparation conditions of the water absorbent resin particles (7) thus obtained are indicated in Table 4, and physical properties of the water absorbent resin particles (7) are indicated in Tables 5 and 6.

Example 8

Operations similar to those of Example 1 were carried out except that a dispersion liquid (8) was used in which the glycerine fatty acid ester (middle purity monoglyceride vegetable olein•stearin) (manufactured by Kao Corporation; product name: EXCEL 122V) was replaced with the same weight of polyoxyethylene stearyl ether (manufactured by Kao Corporation; product name: EMULGEN 306P, HLB=9.4 (catalog value)). Thus, water absorbent resin particles (8) (also referred to as "water absorbing agent (8)") were obtained to which the dispersion liquid containing 100 ppm of a specific surfactant (EMULGEN 306P) had been post-added. Preparation conditions of the water absorbent resin particles (8) thus obtained are indicated in Table 4, and physical properties of the water absorbent resin particles (8) are indicated in Table 5.

Example 9

Operations similar to those of Example 1 were carried out except that a dispersion liquid (9) was used in which the glycerine fatty acid ester (middle purity monoglyceride vegetable olein•stearin) (manufactured by Kao Corporation; product name: EXCEL 122V) was replaced with the same weight of glycerol monostearate (manufactured by Wako Pure Chemical Industries, Ltd., HLB=3.8 (calculated by the Griffin method)). Thus, water absorbent resin particles (9) (also referred to as "water absorbing agent (9)") were obtained to which the dispersion liquid containing 100 ppm of a specific surfactant (glycerol monostearate) had been post-added. Preparation conditions of the water absorbent resin particles (9) thus obtained are indicated in Table 4, and physical properties of the water absorbent resin particles (9) are indicated in Table 5.

Example 10

Operations similar to those of Example 1 were carried out except that a dispersion liquid (10) was used in which 0.5 g of the glycerine fatty acid ester (middle purity monoglyceride vegetable olein•stearin) (manufactured by Kao Corporation; product name: EXCEL 122V) was replaced with a mixture of 0.25 g of glycerol monostearate (manufactured by Wako Pure Chemical Industries, Ltd.) and 0.25 g of glycerol distearate (manufactured by Wako Pure Chemical Industries, Ltd., HLB=2.4 (calculated by the Griffin method)). Thus, water absorbent resin particles (10) (also referred to as "water absorbing agent (10)") were obtained to which the dispersion liquid containing two specific surfactants (i.e., 50 ppm of glycerol monostearate and 50 ppm of glycerol distearate) had been post-added. Preparation conditions of the water absorbent resin particles (10) thus obtained are indicated in Table 4, and physical properties of the water absorbent resin particles (10) are indicated in Table 5.

Example 11

Operations similar to those of Example 1 were carried out except that the added amount of the dispersion liquid (1) of glycerine fatty acid ester (middle purity monoglyceride vegetable olein•stearin) (manufactured by Kao Corporation; product name: EXCEL 122V) relative to 100 parts by weight of the surface crosslinked water absorbent resin particles (1) was changed from 1 part by weight to 0.80 part by weight. Thus, water absorbent resin particles (11) (also referred to as "water absorbing agent (11)") were obtained to which the dispersion liquid containing 80 ppm of a specific surfactant (EXCEL 122V) had been post-added. Preparation conditions of the water absorbent resin particles (11) thus obtained are indicated in Table 4, and physical properties of the water absorbent resin particles (11) are indicated in Tables 5 and 6.

Example 12

0.25 g of glycerine fatty acid ester (middle purity monoglyceride vegetable olein•stearin) (manufactured by Kao Corporation; product name: EXCEL 122V, HLB=3.5 (catalog value)), which served as a surfactant and had been dissolved at 60° C., and 0.25 g of polyoxyethylene sorbitan monostearate (manufactured by Kao Corporation; product name: RHEODOL TW-S120V, HLB=14.9 (catalog value), corresponding to the water-soluble dispersing agent of the present invention), which had been dissolved at 60° C., were put in a polypropylene container having a capacity of 1 liter, and then uniformly mixed. Subsequently, 49.5 g of deionized water (ion-exchanged water) was put in the polypropylene container, and the mixture was stirred with the use of a 50 mm fluorocarbon resin rotor. Thus, a dispersion liquid (12) was obtained in which glycerine fatty acid ester was dispersed.

Next, 1.2 parts by weight of the mixed solution (1) obtained in Example 1 was added, while being stirred, relative to 100 parts by weight of the surface crosslinked water absorbent resin particles (1) obtained in Production Example 1, and mixed for 1 minute. The mixture was placed in a still state at a room temperature for 5 minutes, and then 1.5 parts by weight of the dispersion liquid (12) was further added, while being stirred, relative to 100 parts by weight of the surface crosslinked water absorbent resin particles (1), and mixed for 1 minute. Then, the mixture was dried at 60° C. for 30 minutes under a windless condition, and resultant particles were caused to pass through the JIS standard sieve having a mesh size of 850 μm. Thus, water absorbent resin particles (12) (also referred to as "water absorbing agent (12)") were obtained to which a dispersion liquid containing 75 ppm of the specific surfactant (EXCEL 122V) and 75 ppm of the water-soluble dispersing agent (RHEODOL TW-S120V) had been post-added. Preparation conditions of the water absorbent resin particles (12) thus obtained are indicated in Table 4, and physical properties of the water absorbent resin particles (12) are indicated in Tables 5 and 6.

Example 13

Operations similar to those of Example 12 were carried out except that an added amount of the dispersion liquid (12) thus obtained relative to 100 parts by weight of the surface crosslinked water absorbent resin particles (1) was changed from 1.5 parts by weight to 2.0 parts by weight. Thus, water absorbent resin particles (13) (also referred to as "water absorbing agent (13)") were obtained to which the dispersion liquid containing 100 ppm of the specific surfactant (EXCEL 122V) and 100 ppm of the water-soluble dispersing agent (RHEODOL TW-S120V) had been post-added. Preparation conditions of the water absorbent resin particles (13) thus obtained are indicated in Table 4, and physical properties of the water absorbent resin particles (13) are indicated in Table 5.

Example 14

Operations similar to those of Example 12 were carried out except that, in preparing the dispersion liquid, (i) a used amount of the glycerine fatty acid ester (middle purity monoglyceride vegetable olein•stearin) (manufactured by Kao Corporation; product name: EXCEL 122V) was changed from 0.25 g to 0.45 g and (ii) a used amount of the polyoxyethylene sorbitan monostearate (manufactured by Kao Corporation; product name: RHEODOL TW-S120V) was changed from 0.25 g to 0.05 g. Thus, a dispersion liquid (14) was obtained.

Next, 1.2 parts by weight of the mixed solution (1) obtained in Example 1 was added, while being stirred, relative to 100 parts by weight of the surface crosslinked water absorbent resin particles (1) obtained in Production Example 1, and mixed for 1 minute. The mixture was placed in a still state at a room temperature for 5 minutes, and 0.83 part by weight of the dispersion liquid (14) was added, while being stirred, relative to 100 parts by weight of the surface crosslinked water absorbent resin particles (1), and mixed for 1 minute. Then, the mixture was dried at 60° C. for 30 minutes under a windless condition, and resultant particles were caused to pass through the JIS standard sieve having a mesh size of 850 μm. Thus, water absorbent resin particles (14) (also referred to as "water absorbing agent (14)") were obtained to which a dispersion liquid containing 75 ppm of the specific surfactant (EXCEL 122V) and approximately 8.3 ppm of the water-soluble dispersing agent (RHEODOL TW-S120V) had been post-added. Preparation conditions of the water absorbent resin particles (14) thus obtained are indicated in Table 4, and physical properties of the water absorbent resin particles (14) are indicated in Tables 5 and 6.

Example 15

Operations similar to those of Example 12 were carried out except that, in preparing the dispersion liquid, (i) a used amount of the glycerine fatty acid ester (middle purity monoglyceride vegetable olein•stearin) (manufactured by Kao Corporation; product name: EXCEL 122V) was changed from 0.25 g to 0.05 g and (ii) a used amount of the polyoxyethylene sorbitan monostearate (manufactured by Kao Corporation; product name: RHEODOL TW-S120V) was changed from 0.25 g to 0.45 g. Thus, a dispersion liquid (15) was obtained.

Next, 1.2 parts by weight of the mixed solution (1) obtained in Example 1 was added, while being stirred, relative to 100 parts by weight of the surface crosslinked water absorbent resin particles (1) obtained in Production Example 1, and mixed for 1 minute. The mixture was placed in a still state at a room temperature for 5 minutes. After that, 3.0 parts by weight of the dispersion liquid (15) was added, while being stirred, relative to 100 parts by weight of the surface crosslinked water absorbent resin particles (1), and mixed for 1 minute. Then, the mixture was dried at 60° C. for 30 minutes under a windless condition, and resultant particles were caused to pass through the JIS standard sieve having a mesh size of 850 μm. Thus, water absorbent resin particles (15) (also referred to as "water absorbing agent (15)") were obtained to which a dispersion liquid containing 30 ppm of the specific surfactant (EXCEL 122V) and 270 ppm of the water-soluble dispersing agent (RHEODOL TW-S120V) had been post-added. Preparation conditions of the water absorbent resin particles (15) thus obtained are indicated in Table 4, and physical properties of the water absorbent resin particles (15) are indicated in Table 5.

Example 16

Operations similar to those of Example 12 were carried out except that a dispersion liquid (16) was used in which the polyoxyethylene sorbitan monostearate (manufactured by Kao Corporation; product name: RHEODOL TW-S120V) was replaced with polyoxyethylene hydrogenated castor oil (manufactured by Kao Corporation; product name: EMANON CH-80, HLB=15.0, corresponding to the water-soluble dispersing agent in the present invention). Thus, water absorbent resin particles (16) (also referred to as "water absorbing agent (16)") were obtained to which a dispersion liquid containing 75 ppm of the specific surfactant (EXCEL 122V) and 75 ppm of the water-soluble dispersing agent (EMANON CH-80) had been post-added. Preparation conditions of the water absorbent resin particles (16) thus obtained are indicated in Table 4, and physical properties of the water absorbent resin particles (16) are indicated in Tables 5 and 6.

Example 17

Operations similar to those of Example 12 were carried out except that a dispersion liquid (17) was used in which the polyoxyethylene sorbitan monostearate (manufactured by Kao Corporation; product name: RHEODOL TW-S120V) was replaced with sodium salt of a β-naphthalene sulfonic acid formalin condensate (manufactured by Kao Corporation; product name: DEMOL N, corresponding to the water-soluble dispersing agent in the present invention). Thus, water absorbent resin particles (17) (also referred to as "water absorbing agent (17)") were obtained to which a dispersion liquid containing 75 ppm of the specific surfactant (EXCEL 122V) and 75 ppm of the water-soluble dispersing agent (DEMOL N) had been post-added. Preparation conditions of the water absorbent resin particles (17) thus obtained are indicated in Table 4, and physical properties of the water absorbent resin particles (17) are indicated in Tables 5 and 6.

Example 18

Operations similar to those of Example 12 were carried out except that a dispersion liquid (18) was used in which the polyoxyethylene sorbitan monostearate (manufactured by Kao Corporation; product name: RHEODOL TW-S120V) was replaced with sodium alginate (corresponding to the water-soluble dispersing agent of the present invention, manufactured by KANTO CHEMICAL CO., INC.). Thus, water absorbent resin particles (18) (also referred to as "water absorbing agent (18)") were obtained to which a dispersion liquid containing 75 ppm of the specific surfactant (EXCEL 122V) and 75 ppm of the water-soluble dispersing agent (sodium alginate) had been post-added. Preparation conditions of the water absorbent resin particles (18) thus obtained are indicated in Table 4, and physical properties of the water absorbent resin particles (18) are indicated in Tables 5 and 6.

Example 19

Operations similar to those of Example 12 were carried out except that a dispersion liquid (19) was used in which the polyoxyethylene sorbitan monostearate (manufactured by Kao Corporation; product name: RHEODOL TW-S120V) was replaced with decaglycerine laurate (manufactured by RIKEN VITAMIN Co., Ltd.; product name: POEM J-0021, HLB=15.5 (catalog value), corresponding to the water-soluble dispersing agent in the present invention). Thus, water absorbent resin particles (19) (also referred to as "water absorbing agent (19)") were obtained to which 75 ppm of the specific surfactant (EXCEL 122V) and 75 ppm of the water-soluble dispersing agent (POEM J-0021) had been added. Preparation conditions of the water absorbent resin particles (19) thus obtained are indicated in Table 4, and physical properties of the water absorbent resin particles (19) are indicated in Tables 5 and 6.

Example 20

Operations similar to those of Example 1 were carried out except that the mixed solution (1) as a liquid permeability improving agent was not added. Thus, water absorbent resin particles (20) (also referred to as "water absorbing agent (20)") were obtained to which 100 ppm of the specific surfactant (EXCEL 122V) had been added. Preparation conditions of the water absorbent resin particles (20) thus obtained are indicated in Table 4, and physical properties of the water absorbent resin particles (20) are indicated in Tables 5 and 6. Note that a bulk specific gravity of the surface crosslinked water absorbent resin particles (1) was 0.65 g/mL.

Example 21

Operations similar to those of Example 20 were carried out except that the base water absorbent resin particles (1) obtained in Production Example 1 was used instead of the surface crosslinked water absorbent resin particles (1), and thus water absorbent resin particles (21) (also referred to as "water absorbing agent (21)") were obtained to which a dispersion liquid containing 100 ppm of a specific surfactant (EXCEL 122V) had been post-added. Preparation conditions of the water absorbent resin particles (21) thus obtained are indicated in Table 4, and physical properties of the water absorbent resin particles (21) are indicated in Table 5. Note that a bulk specific gravity of the base water absorbent resin particles (1) was 0.57 g/mL.

Example 22

Operations similar to those of Example 4 were carried out except that, after the dispersion liquid (4) was added, the mixture was put in a 250 ml lidded polypropylene container and left for 18 hours at a room temperature (i.e., at a temperature of 23.5° C. and at a relative humidity of 38%) instead of being dried for 30 minutes at 60° C. under the windless condition. Thus, water absorbent resin particles (22) (also referred to as "water absorbing agent (22)") were obtained to which the dispersion liquid containing 100 ppm of the specific surfactant (EXCEL S-95) had been post-added. Preparation conditions of the water absorbent resin particles (22) thus obtained are indicated in Table 4, and physical properties of the water absorbent resin particles (22) are indicated in Table 5.

Comparative Example 6

0.2 g of polyoxyethylene sorbitan monostearate (manufactured by Kao Corporation; product name: RHEODOL TW-S120V, HLB=14.9 (catalog value)), which served as a surfactant and had been melted at 60° C., and 19.8 g of deionized water (ion-exchanged water) were put in a 250 ml polypropylene container and were mixed with the use of a 30 mm fluorocarbon resin rotor while being heated in a hot water bath at approximately 65° C. Thus, a comparative aqueous solution (6) was prepared.

Next, 1.2 parts by weight of the mixed solution (1) obtained in Example 1 was added, while being stirred, relative to 100 parts by weight of the surface crosslinked water absorbent resin particles (1) obtained in Production Example 1, and mixed for 1 minute. After the mixture was placed in a still state at a room temperature for 5 minutes, 1 part by weight of the comparative aqueous solution (6) was further added, while being stirred, relative to 100 parts by weight of the surface crosslinked water absorbent resin particles (1), and mixed for 1 minute. Next, the mixture was dried at 60° C. for 30 minutes under a windless condition, and resultant particles were caused to pass through the JIS standard sieve having a mesh size of 850 µm. Thus, comparative water absorbent resin particles (6) (also referred to as "comparative water absorbing agent (6)") were obtained to which an aqueous solution containing 100 ppm of the surfactant (RHEODOL TW-S120V), which did not fall within the definition of the surfactant used in the method of the present invention described in this specification, had been added.

Preparation conditions of the comparative water absorbent resin particles (6) thus obtained are indicated in Table 4, and physical properties of the comparative water absorbent resin particles (6) are indicated in Tables 5 and 6.

Comparative Example 7

Operations similar to those of Comparative Example 6 were carried out except that the polyoxyethylene sorbitan monostearate (manufactured by Kao Corporation; product name: RHEODOL TW-S120V) was replaced with the same weight of polyoxyethylene hydrogenated castor oil (manufactured by Kao Corporation; product name: EMANON CH-80, HLB=15.0 (catalog value)). Thus, comparative water absorbent resin particles (7) (also referred to as "comparative water absorbing agent (7)") were obtained to which an aqueous solution containing 100 ppm of the surfactant (EMANON CH-80), which did not fall within the definition of the surfactant used in the method of the present invention described in this specification, had been added. Preparation conditions of the comparative water absorbent resin particles (7) thus obtained are indicated in Table 4, and physical properties of the comparative water absorbent resin particles (7) are indicated in Tables 5 and 6.

Comparative Example 8

Operations similar to those of Example 1 were carried out except that, in preparing the dispersion liquid (1), ethyl alcohol at 23° C. instead of the deionized water at 75° C. as a solvent was stirred at a room temperature with the use of a 30 mm fluorocarbon resin rotor instead of the homogenizer as a stirring method. Thus, a comparative solution (8) was obtained instead of the dispersion liquid (1). The comparative solution (8) was a solution in which glycerine fatty acid ester was uniformly dissolved.

Next, 1.2 parts by weight of the mixed solution (1) obtained in Example 1 was added, while being stirred, relative to 100 parts by weight of the surface crosslinked water absorbent resin particles (1) obtained in Production Example 1, and mixed for 1 minute. The mixture was placed in a still state at a room temperature for 5 minutes, and then 1 part by weight of the comparative solution (8) was further added, while being stirred, relative to 100 parts by weight of the surface crosslinked water absorbent resin particles (1), and mixed for 1 minute. Then, the mixture was dried at 60° C. for 30 minutes under a windless condition, and resultant particles were caused to pass through the JIS standard sieve having a mesh size of 850 µm. Thus, comparative water absorbent resin particles (8) (also referred to as "comparative water absorbing agent (8)") were obtained to which an ethyl alcohol solution containing 100 ppm of a specific surfactant (EXCEL 122V) had been added. Preparation conditions of the comparative water absorbent resin particles (8) thus obtained are indicated in Table 4, and physical properties of the comparative water absorbent resin particles (8) are indicated in Tables 5 and 6.

Comparative Example 9

Operations similar to those of Example 1 were carried out except that an added amount of the dispersion liquid (1) of glycerine fatty acid ester (middle purity monoglyceride vegetable olein•stearin) (manufactured by Kao Corporation; product name: EXCEL 122V) relative to 100 parts by weight of the surface crosslinked water absorbent resin particles (1) was changed from 1 part by weight to 0.20 part by weight. Thus, comparative water absorbent resin particles (9) (also referred to as "comparative water absorbing agent (9)") were obtained to which a dispersion liquid containing 20 ppm of the specific surfactant (EXCEL 122V) had been added. Preparation conditions of the comparative water absorbent resin particles (9) thus obtained are indicated in Table 4, and physical properties of the comparative water absorbent resin particles (9) are indicated in Tables 5 and 6.

Comparative Example 10

Operations similar to those of Example 15 were carried out except that an added amount of the dispersion liquid (15) relative to 100 parts by weight of the surface crosslinked water absorbent resin particles (1) was changed from 3.0 parts by weight to 1.0 part by weight. Thus, comparative water absorbent resin particles (10) (also referred to as "comparative water absorbing agent (10)") were obtained to which a dispersion liquid (water-soluble dispersing agent (RHEODOL TW-S120V)) containing 10 ppm of the specific surfactant (EXCEL 122V) had been added. Preparation conditions of the comparative water absorbent resin particles

(10) thus obtained are indicated in Table 4, and physical properties of the comparative water absorbent resin particles (10) are indicated in Table 5.

Comparative Example 11

1.2 parts by weight of the mixed solution (1) obtained in Example 1 was added, while being stirred, relative to 100 parts by weight of the surface crosslinked water absorbent resin particles (1) obtained in Production Example 1, and mixed for 1 minute. The mixture was placed in a still state at a room temperature for 5 minutes, and then 1 part by weight of glycerine fatty acid ester (middle purity monoglyceride vegetable olein•stearin) (manufactured by Kao Corporation; product name: EXCEL 122V), which served as a surfactant and had been dissolved at 60° C., was added in undiluted form, while being stirred, relative to 100 parts by weight of the surface crosslinked water absorbent resin particles (1) obtained in Production Example 1, and mixed for 1 minute. Then, the mixture was dried at 60° C. for 30 minutes under a windless condition, and resultant particles were caused to pass through the JIS standard sieve having a mesh size of 850 µm. Thus, comparative water absorbent resin particles (11) (also referred to as "comparative water absorbing agent (11)") were obtained. Preparation conditions of the comparative water absorbent resin particles (11) thus obtained are indicated in Table 4, and physical properties of the comparative water absorbent resin particles (11) are indicated in Table 5.

Comparative Example 12

Instead of (i) adding 1.2 parts by weight of the mixed solution (1) obtained in Example 1, while stirring, relative to 100 parts by weight of the surface crosslinked water absorbent resin particles (1) obtained in Production Example 1 and mixing for 1 minute, (ii) placing the mixture in a still state at a room temperature for 5 minutes, and then (iii) adding 1 part by weight of the dispersion liquid (1) obtained in Example 1 relative to 100 parts by weight of the surface crosslinked water absorbent resin particles (1) while stirring and mixing for 1 minute, the adding order of the mixed solution (1) and the dispersion liquid (1) was switched between these.

In other words, operations similar to those of Example 1 were carried out except that (i) 1 part by weight of the dispersion liquid (1) obtained in Example 1 was added, while being stirred, relative to 100 parts by weight of the surface crosslinked water absorbent resin particles (1) obtained in Production Example 1, and uniformly mixed for 1 minute, (ii) the mixture was placed in a still state at a room temperature for 5 minutes, and then (iii) 1.2 parts by weight of the mixed solution (1) of the water-soluble polyvalent metal salt obtained in Example 1 was added, while being stirred, relative to 100 parts by weight of the surface crosslinked water absorbent resin particles (1), and mixed for 1 minute. Thus, comparative water absorbent resin particles (12) (also referred to as "comparative water absorbing agent (12)") were obtained with which the dispersion liquid containing 100 ppm of the specific surfactant (EXCEL 122V) had been mixed before adding the water-soluble polyvalent metal salt. Preparation conditions of the comparative water absorbent resin particles (12) thus obtained are indicated in Table 4, and physical properties of the comparative water absorbent resin particles (12) are indicated in Tables 5 and 6.

Comparative Example 13

A comparative mixed solution (13) was prepared by mixing 12.0 g of the dispersion liquid (1) and 10.0 g of the mixed solution (1) of the water-soluble polyvalent metal salt, which had been obtained in Example 1.

Next, 2.2 parts by weight of the comparative mixed solution (13) was added, while being stirred, relative to 100 parts by weight of the surface crosslinked water absorbent resin particles (1) obtained in Production Example 1, and mixed for 1 minute. Then, the mixture was dried at 60° C. for 30 minutes under a windless condition, and resultant particles were caused to pass through the JIS standard sieve having a mesh size of 850 µm. Thus, comparative water absorbent resin particles (13) (also referred to as "comparative water absorbing agent (13)") were obtained in which 100 ppm of the specific surfactant (EXCEL 122V) and the water-soluble polyvalent metal salt had been mixed simultaneously. Preparation conditions of the comparative water absorbent resin particles (13) thus obtained are indicated in Table 4, and physical properties of the comparative water absorbent resin particles (13) are indicated in Tables 5 and 6.

Comparative Example 14

A surface crosslinking agent, which was a mixed solution containing 0.4 part by weight of ethylenecarbonate, 0.6 part by weight of propyleneglycol, 1.51 parts by weight of deionized water, 0.001 part by weight (i.e., 10 ppm relative to water absorbent resin particles) of polyoxyethylene (20) sorbitan monostearate (manufactured by Kao Corporation; product name: RHEODOL TW-S120V, HLB=14.9 (catalog value)), and 1.0 part by weight of the dispersion liquid (1) obtained in Example 1, was added, while being stirred, relative to 100 parts by weight of the base water absorbent resin particles (1) obtained in Production Example 1, and mixed for 1 minute. The mixture was surface-crosslinked by heating treatment at 180° C. for 45 minutes. After the heating treatment, the resultant water absorbent resin particles were crushed to a size with which the water absorbent resin particles passed through the JIS standard sieve having a mesh size of 850 µm. Thus, comparative surface crosslinked water absorbent resin particles (14) were obtained.

Next, 1.2 parts by weight of the mixed solution (1) prepared in Example 1 was added, while being stirred, relative to 100 parts by weight of the comparative surface crosslinked water absorbent resin particles (14), and mixed for 1 minute. Then, the mixture was dried at 60° C. for 30 minutes under a windless condition, and resultant particles were caused to pass through the JIS standard sieve having a mesh size of 850 µm. Thus, comparative water absorbent resin particles (14) (also referred to as "comparative water absorbing agent (14)") were obtained in which 100 ppm of the specific surfactant (EXCEL 122V) and the surface crosslinking agent had been mixed simultaneously. Preparation conditions of the comparative water absorbent resin particles (14) thus obtained are indicated in Table 4, and physical properties of the comparative water absorbent resin particles (14) are indicated in Tables 5 and 6.

Comparative Example 15

When the dispersion liquid (1) was prepared in Example 1, mixing was carried out with the use of a fluorocarbon resin rotor at a room temperature, instead of using the homogenizer. As a result, no dispersion liquid was obtained and a comparative mixed solution (15) was obtained in which phase separation occurred within less than 1 minute. Operations similar to those of Example 1 were carried out except that the comparative mixed solution (15) was used instead of the dispersion liquid (1), and thus comparative water absorbent resin particles (15) (also referred to as "comparative water absorbing agent (15)") were obtained. Note that, when the comparative mixed solution (15) was added to the surface crosslinked water absorbent resin particles (1), a predetermined amount of the comparative mixed solution (15) was sampled within 30 seconds after the comparative mixed solution (15) was stirred with the use of the fluorocarbon resin rotor, such that samples were taken from respective phases as evenly as possible. Preparation conditions of the comparative water absorbent resin particles (15) thus obtained are indicated in Table 4, and physical properties of the comparative water absorbent resin particles (15) are indicated in Table 5.

Comparative Example 16

In conformity with Patent Literature WO2005/075070, zinc stearate was added.

That is, in a dual arm kneader which was made of stainless steel and was provided with a jacket and two sigma blades, 0.10 mol % of polyethylene glycol diacrylate was dissolved in a sodium acrylate aqueous solution having a neutralization ratio of 71.3 mol %, and thus a reaction solution was prepared. Next, the reaction solution deaerated with nitrogen gas. Subsequently, a 10 wt % of sodium persulfate aqueous solution and a 0.1 wt % of L-ascorbic acid aqueous solution were added, while being stirred, to the reaction solution, and polymerization started after approximately 1 minute. Then, polymerization was carried out while crushing the generated gel, and a gel-like hydrated polymer was obtained 20 minutes after the polymerization started. The hydrate polymer thus obtained was grain-refined to have a diameter of approximately 5 mm or less.

The hydrated polymer thus grain-refined was dried by hot air at 170° C. for 50 minutes. The dried matter was pulverized by the use of a roll mill, and further classified with the use of a JIS standard sieve having a mesh size of 850 μm and a JIS standard sieve having a mesh size of 150 μm. Thus, base polymer powder was obtained which passed through the sieve of 850 μm but did not pass through the sieve of 150 μm. A surface treatment agent made up of a mixed solution containing 0.5 part by weight of 1,4-butanediol, 1.0 part by weight of propyleneglycol, and 3.0 parts by weight of water was mixed with 100 parts by weight of the base polymer powder thus obtained. After that, the mixture was subjected to heating treatment at 210° C. for approximately 30 minutes, and thus comparative surface crosslinked water absorbent resin particles (16) were obtained.

100 g of the comparative surface crosslinked water absorbent resin particles (16) and 0.6 mg of zinc stearate (StZn) were put in a 500 ml plastic container and mixed by shaking the plastic container. Thus, comparative water absorbent resin particles (16) (also referred to as "comparative water absorbing agent (16)") were obtained. Preparation conditions of the comparative water absorbent resin particles (16) thus obtained are indicated in Table 4, and physical properties of the comparative water absorbent resin particles (16) are indicated in Tables 5 and 6.

Comparative Example 17

In conformity with Patent Literature 37 (WO2008/055935, U.S. Pat. No. 8,017,549), PEG-400 (i.e., polyethylene glycol having an average molecular weight of 400 g/mol) was added.

That is, 1.2 parts by weight of the mixed solution (1) obtained in Example 1 was added, while being stirred, relative to 100 parts by weight of the comparative surface crosslinked water absorbent resin particles (16) obtained in Comparative Example 16, and mixed for 1 minute. Then, the mixture was dried at 60° C. for 30 minutes under a windless condition, and resultant particles were caused to pass through the JIS standard sieve having a mesh size of 850 μm. Thus, comparative liquid permeability enhanced water absorbent resin particles (17) were obtained.

Next, a mixture of 0.28 part by weight of deionized water and 0.07 part by weight of PEG-400 was added, while being stirred, relative to 100 parts by weight of the comparative liquid permeability enhanced water absorbent resin particles (17), and mixed for 1 minute. Thus, comparative water absorbent resin particles (17) (also referred to as "comparative water absorbing agent (17)") were obtained. Preparation conditions of the comparative water absorbent resin particles (17) thus obtained are indicated in Table 4, and physical properties of the comparative water absorbent resin particles (17) are indicated in Tables 5 and 6.

Comparative Example 18

In conformity with Japanese Patent Application Tokugan No. 2011-077349 which is an earlier application, zinc stearate and a surfactant were added.

That is, 0.706 part by weight of zinc stearate water-dispersion (manufactured by ADEKA CHEMICAL SUPPLY CO., LTD.; product name: EFUKODHISUPA (Registered Trademark)/solid content of 42.5 wt %, containing a surfactant) and 6.254 parts by weight of water were mixed with each other, and then 0.04 part by weight of ethylenediamine tetra(methylenephosphonic acid)-5 sodium (hereinafter, abbreviated to "EDTMP.5Na") was added. Thus, a comparative dispersion liquid (18) was prepared.

Next, 7 parts by weight of the comparative dispersion liquid (18) (i.e., virtual added amount; 0.3 part by weight of zinc stearate, 0.04 part by weight of EDTMP.5Na, 6.66 parts by weight of water) was added, while being stirred, relative to 100 parts by weight of the surface crosslinked water absorbent resin particles (1) obtained in Production Example (1), and mixed for 1 minute. Then, the mixture was put in a reclosable bag and the reclosable bag is then sealed. The mixture was hardened at 80° C. for 1 hour and then crushed to a size with which the mixture passed through the JIS standard sieve having a mesh size of 850 μm. Thus, comparative water absorbent resin particles (A18) were obtained. Further, a comparative surfactant aqueous solution (18) was prepared which contained 0.1 part by weight of polyoxyethylene alkyl ether (manufactured by Nippon Shokubai Co., Ltd.; SOFTANOL 90 (Registered Trademark)/solid content of 100 wt %, HLB=13.3 (Griffin method)) and 2.0 parts by weight of water. 2.1 parts by weight of the comparative surfactant aqueous solution (18) was added, while being stirred, relative to 100 parts by weight of the comparative water absorbent resin particles (A18), and mixed for 1 minute. Then, the mixture was put in a reclosable bag and the reclosable bag is then sealed. The mixture was hardened at 80° C. for 1 hour and then crushed to a size with which the mixture passed through the JIS standard sieve having a mesh size of 850 μm. Thus, comparative water absorbent resin particles (18) (also referred to as "comparative water absorbing agent (18)") were obtained. Preparation conditions of the comparative water absorbent resin particles (18) thus obtained are indicated in Table 4, and physical properties of the comparative water absorbent resin particles (18) are indicated in Tables 5 and 6.

Comparative Example 19

In conformity with Patent Literature 39 (pamphlet of International Publication No. 2011/040472) which is an earlier application of Patent Literature 38 (Japanese Patent Application Tokugan No. 2011-077349) described in Comparative Example 18, metallic soap and a surfactant were simultaneously added as a dispersion liquid.

That is, instead of preparing the comparative surfactant aqueous solution (18) in Comparative Example 18, a comparative dispersion liquid (19) was prepared by mixing 2.353 parts by weight of zinc stearate water-dispersion and 4.207 parts by weight of water, and then adding 0.04 part by weight of EDTMP.5Na and 0.4 part by weight of sodium polyoxyethylene lauryl sulfate (manufactured by Kao Corporation; EMAL 20C/solid content of 25 wt %) to the mixture.

Next, operations similar to those of Comparative Example 18 were carried out except that 7.0 parts by weight of the comparative dispersion liquid (19) (i.e., virtual added amount; 1.0 part by weight of zinc stearate, 0.04 part by weight of EDTMP.5Na, 0.1 part by weight of sodium polyoxyethylene lauryl sulfate, and 5.86 parts by weight of water) was added, while being stirred, relative to 100 parts by weight of the surface crosslinked water absorbent resin particles (1) obtained in Production Example (1). Thus, comparative water absorbent resin particles (19) (also referred to as "comparative water absorbing agent (19)") were obtained. Preparation conditions of the comparative water absorbent resin particles (19) thus obtained are indicated in Table 4, and physical properties of the comparative water absorbent resin particles (19) are indicated in Tables 5 and 6.

Example 23

Operations similar to those of Comparative Example 14 were carried out except that the mixed solution (1) was not added. Thus, water absorbent resin particles (23) (also referred to as "water absorbing agent (23)") were obtained to which 100 ppm of the specific surfactant (EXCEL 122V) and the surface crosslinking agent had been added. Preparation conditions of the water absorbent resin particles (23) thus obtained are indicated in Table 4, and physical properties of the water absorbent resin particles (23) are indicated in Tables 5 and 6.

Example 24

Operations similar to those of Example 23 were carried out except that, in preparing the dispersion liquid (1), a dispersion liquid (24) was used in which the glycerine fatty acid ester (middle purity monoglyceride vegetable olein•stearin) (manufactured by Kao Corporation; product name: EXCEL 122V) was replaced with the same weight of glycerine fatty acid ester (glycerol monostearate) (manufactured by Kao Corporation; product name: RHEODOL MS-60, HLB=3.5 (catalog value)). Thus, water absorbent resin particles (24) (also referred to as "water absorbing agent (24)") were obtained to which 100 ppm of the specific surfactant (RHEODOL MS-60) and the surface crosslinking agent had been added. Preparation conditions of the water absorbent resin particles (24) thus obtained are indicated in Table 4, and physical properties of the water absorbent resin particles (24) are indicated in Tables 5 and 6.

Example 25

Operations similar to those of Example 23 were carried out except that the dispersion liquid (14) prepared in Example 14 was used instead of the dispersion liquid (1). Thus, water absorbent resin particles (25) (also referred to as "water absorbing agent (25)") to which 100 ppm of the specific surfactant (EXCEL 122V) and the surface crosslinking agent had been added. Preparation conditions of the water absorbent resin particles (25) thus obtained are indicated in Table 4, and physical properties of the water absorbent resin particles (25) are indicated in Tables 5 and 6.

Comparative Example 20

421.9 g of acrylic acid, 2.60 g of polyethylene glycol diacrylate (molecular weight of 523) as an internal crosslinking agent, 113.5 g of a 0.1 wt % of diethylenetriamine pentaacetic acid-3 sodium aqueous solution, 173.8 g of a 48.5 wt % of sodium hydroxide aqueous solution, 0.44 g of a 10.0 wt % of polyoxyethylene (20) sorbitan monostearate (manufactured by Kao Corporation) aqueous solution, and 290.5 g of deionized water (ion-exchanged water) were put in a polypropylene container having a capacity of 2 liters and were dissolved (mixed). Thus, a comparative monomer aqueous solution (20) was prepared. A temperature of the comparative monomer aqueous solution (20) rose to 64° C. by heat of a first stage neutralization immediately after the preparation.

Next, 835 g of the comparative monomer aqueous solution (20) was put in a polypropylene container having a capacity of 2 liters, and was cooled down while being stirred. At a time point at which a temperature of the solution became 53° C., 148.9 g of a 48.5 wt % of sodium hydroxide aqueous solution, whose temperature had been adjusted to 30° C., was added and mixed, and thus a comparative monomer aqueous solution (20') was prepared. At this time, a temperature of the comparative monomer aqueous solution (20') rose to 83.1° C. by heat of a second stage neutralization immediately after the preparation. The comparative monomer aqueous solution (20') containing the surfactant became whitish because extremely small gas bubbles were introduced due to decrease in gas solubility caused by the temperature rise.

Next, at a time point at which the temperature of the comparative monomer aqueous solution (20') decreased to 83° C., nitrogen gas was introduced to the comparative monomer aqueous solution (20') at 1 L/min for 5 seconds with the use of Kinoshita glass ball filter (filter particle No. 4) manufactured by Kinoshita Rika Kogyo Co., Ltd. Further, 15.3 g of a 3.8 wt % of sodium persulfate aqueous solution was added, while being stirred, to the comparative monomer aqueous solution (20') and, immediately after that, the mixture was poured to a stainless steel vat container (with bottom surface of 340 mm×340 mm, height of 25 mm, inner face coated with Teflon (Registered Trademark)) in an atmospheric air open system. Note that the vat container was heated up until a surface temperature was increased to 40° C. with the use of a hot plate (manufactured by Iuchi Seieido Co., Ltd.; NEO HOTPLATE HI-1000).

Polymerization reaction started 10 seconds after the comparative monomer aqueous solution (20') was poured to the vat container. The polymerization reaction progressed while (i) generating water vapor and (ii) swelling and foaming vertically and horizontally, and then shrunk to a size which was slightly larger than the vat container. The swelling and shrinking ended within approximately 1 minute. After 3 minutes elapsed from when the polymerization reaction started, a water-containing gel-like crosslinked polymer (hydrogel) was obtained. Note that these operations were carried out in an atmospheric air open system, and a peak temperature in polymerization was 113° C.

The water-containing gel-like crosslinked polymer (hydrogel) obtained by the polymerization reaction was crushed with the use of a meat chopper (manufactured by Iizuka Kogyo Co., Ltd., MEAT-CHOPPER TYPE: 12VR-400KSOX, die pore diameter: 6.4 mm, the number of pores: 38, die thickness: 8 mm), and a grain-refined water-containing gel-like crosslinked polymer was obtained. In this case, an input of the hydrogel was 350 [g/min], and the crushing was carried out while also adding, at 80 [g/min], deionized water whose temperature had been adjusted to 90° C., simultaneously with the adding of the hydrogel.

The grain-refined water-containing gel-like crosslinked polymer obtained in the crushing operation was spread on woven stainless-steel wires having a mesh size of 850 μm, and dried by hot air at 180° C. for 30 minutes. Next, a dried matter thus obtained by the drying operation was pulverized with the use of a roll mill (manufactured by Inoguchi Giken Ltd., WML-type roll crusher) and was then classified with the use of a JIS standard sieve having a mesh size of 850 μm and a JIS standard sieve having a mesh size of 45 μm.

By the above described set of operations, irregularly pulverized comparative base water absorbent resin particles (20) were obtained which had a solid content of 96 wt %, a weight average particle diameter (D50) of 448 μm, and a logarithmic standard deviation (σζ) of particle size distribution of 0.36.

A surface crosslinking agent made up of a mixed solution containing 0.4 part by weight of ethylenecarbonate, 0.6 part by weight of propyleneglycol, 2.5 parts by weight of deionized water, and 0.001 part by weight (i.e., 10 ppm relative to comparative base water absorbent resin particles) of polyoxyethylene (20) sorbitan monostearate (manufactured by Kao Corporation) was uniformly mixed with 100 parts by weight of the comparative base water absorbent resin particles (20) thus obtained, and then the mixture was surface-crosslinked by heating treatment at 180° C. for 45 minutes. After the heating treatment, the comparative surface crosslinked water absorbent resin particles thus obtained were crushed to a size with which the comparative surface crosslinked water absorbent resin particles passed through the JIS standard sieve having a mesh size of 850 μm. Thus, comparative surface crosslinked water absorbent resin particles (20) were obtained.

Next, 1.2 parts by weight of the mixed solution (1) obtained in Example 1 was added, while being stirred, relative to 100 parts by weight of the comparative surface crosslinked water absorbent resin particles (20) and uniformly mixed for 1 minute. Then, the mixture was dried at 60° C. for 30 minutes under a windless condition, and resultant particles were caused to pass through the JIS standard sieve having a mesh size of 850 μm. Thus, comparative water absorbent resin particles (20) (also referred to as "comparative water absorbing agent (20)") were obtained. Preparation conditions of the comparative water absorbent resin particles (20) thus obtained are indicated in Table 4, and physical properties of the comparative water absorbent resin particles (20) are indicated in Tables 5 and 6.

Example 26

Operations similar to those of Comparative Example 20 were carried out except that 1.2 parts by weight of the mixed solution (1) obtained in Example 1 was added, while being stirred, relative to 100 parts by weight of the comparative surface crosslinked water absorbent resin particles (20), and mixed for 1 minute. The mixture was placed in a still state at a room temperature for 5 minutes, and then 1 part by weight of the dispersion liquid (1) was added relative to 100 parts by weight of the comparative surface crosslinked water absorbent resin particles (20) and uniformly mixed. Thus, water absorbent resin particles (26) (also referred to as "water absorbing agent (26)") were obtained to which 100 ppm of the specific surfactant (EXCEL 122V) and the surface crosslinking agent had been added. Preparation conditions of the water absorbent resin particles (26) thus obtained are indicated in Table 4, and physical properties of the water absorbent resin particles (26) are indicated in Tables 5 and 6.

Example 27

421.9 g of acrylic acid, 1.38 g of polyethylene glycol diacrylate (molecular weight of 523) as an internal crosslinking agent, 113.5 g of a 0.1 wt % of diethylenetriamine pentaacetic acid-3 sodium aqueous solution, 173.8 g of a 48.5 wt % of sodium hydroxide aqueous solution, 0.44 g of a 10.0 wt % of polyoxyethylene (20) sorbitan monostearate (manufactured by Kao Corporation) aqueous solution as a surfactant, and 291.7 g of deionized water (ion-exchanged water) were put in a polypropylene container having a capacity of 2 liters and were dissolved (mixed). Thus, a monomer aqueous solution (27) was prepared. A temperature of the aqueous solution (27) rose to 64° C. by heat of a first stage neutralization immediately after the preparation.

Next, 835 g of the monomer aqueous solution (27) was put in a polypropylene container having a capacity of 2 liters and was cooled down while being stirred. At a time point at which a temperature of the solution became 53° C., 148.9 g of a 48.5 wt % of sodium hydroxide aqueous solution, whose temperature had been adjusted to 30° C., was added and mixed, and thus a monomer aqueous solution (27') was prepared. At this time, a temperature of the monomer aqueous solution (27') rose to 83.1° C. by heat of a second stage neutralization immediately after the preparation. The monomer aqueous solution (27') containing the surfactant became whitish because extremely small gas bubbles were introduced due to decrease in gas solubility caused by the temperature rise.

Next, at a time point at which the temperature of the monomer aqueous solution (27') decreased to 83° C., nitrogen gas was introduced to the monomer aqueous solution (27') at 1 L/min for 5 seconds with the use of Kinoshita glass ball filter (filter particle No. 4) manufactured by Kinoshita Rika Kogyo Co., Ltd. Further, 15.3 g of a 3.8 wt % of sodium persulfate aqueous solution was added, while being stirred, to the monomer aqueous solution (27') and, immediately after that, the mixture was poured to a stainless steel vat container (with bottom surface of 340 mm×340 mm, height of 25 mm, inner face coated with Teflon (Registered Trademark)) in an atmospheric air open system. Note that the vat container was heated up until a surface temperature was increased to 40° C. with the use of a hot plate (manufactured by Iuchi Seieido Co., Ltd.; NEO HOTPLATE HI-1000).

Polymerization reaction started 10 seconds after the monomer aqueous solution (27') was poured to the vat container. The polymerization reaction progressed while (i) generating water vapor and (ii) swelling and foaming vertically and horizontally, and then shrunk to a size which was slightly larger than the vat container. The swelling and shrinking ended within approximately 1 minute. After 3 minutes elapsed from when the polymerization reaction started, a water-containing gel-like crosslinked polymer (hydrogel) was obtained. Note that the set of operations was carried out in an atmospheric air open system, and a peak temperature in polymerization was 113° C.

Subsequently, operations of crushing, drying, pulverization, and classification similar to those of Comparative Example 20 were carried out relative to the water-containing gel-like crosslinked polymer (hydrogel) thus obtained. By the operations, irregularly pulverized base water absorbent resin particles (27) were obtained which had a solid content of 96 wt %, a weight average particle diameter (D50) of 354 μm, and a logarithmic standard deviation (σζ) of particle size distribution of 0.36.

A surface crosslinking agent made up of a mixed solution containing 0.024 part by weight of ethylene glycol diglycidyl ether, 0.31 part by weight of ethylenecarbonate, 0.52 part by weight of propyleneglycol, and 2.1 parts by weight of deionized water was uniformly mixed with 100 parts by weight of the base water absorbent resin particles (27) thus obtained, and then the mixture was surface-crosslinked by heating treatment at 195° C. for 25 minutes. After the heating treatment, the surface crosslinked water absorbent resin particles thus obtained were crushed to a size with which the surface crosslinked water absorbent resin particles passed through the JIS standard sieve having a mesh size of 850 μm. Thus, surface crosslinked water absorbent resin particles (27) were obtained.

Next, 1.2 parts by weight of the mixed solution (1) obtained in Example 1 was added, while being stirred, relative to 100 parts by weight of the surface crosslinked water absorbent resin particles (27), and uniformly mixed for 1 minute. The mixture was placed in a still state at a room temperature for 5 minutes, and then 1 part by weight of the dispersion liquid (1) obtained in Example 1 was further added relative to 100 parts by weight of the surface crosslinked water absorbent resin particles (27) and uniformly mixed. Then, the mixture was dried at 60° C. for 30 minutes under a windless condition, and resultant particles were caused to pass through the JIS standard sieve having a mesh size of 850 μm. Thus, water absorbent resin particles (27) (also referred to as "water absorbing agent (27)") were obtained. Preparation conditions of the water absorbent resin particles (27) thus obtained are indicated in Table 4, and physical properties of the water absorbent resin particles (27) are indicated in Tables 5 and 6.

TABLE 1

MOISTURE CONTENT AND DAMAGE RESISTANCE/BULK SPECIFIC GRAVITY PREPARATION CONDITIONS

| | Surfactant whose HLB is 10 or less | | |
|---|---|---|---|
| | Name | Added Amount (ppm) | Added Amount of Water (%) |
| Example 1 | EXCEL 122V | 100 | 0.99 |
| Example 2 | EXCEL 122V | 100 | 1.99 |
| Com. Ex. 1 | — | — | 0 |
| Com. Ex. 2 | — | — | 1 |
| Com. Ex. 3 | — | — | 5 |
| Com. Ex. 4 | EXCEL 122V | 100 | 3.99 |
| Com. Ex. 5 | EXCEL 122V | 100 | 9.99 |

Com. Ex.: Comparative Example

TABLE 2

PHYSICAL PROPERTIES SUCH AS MOISTURE CONTENT, DAMAGE RESISTANCE, BULK SPECIFIC GRAVITY AND POWDER CHARACTERISTICS

| | Surfactant whose ELB is 10 or less | | Bulk Specific Gravity (g/ml) | Hausner Ratio | Loose Bulk Specific Gravity (g/ml) | Tight Bulk Specific Gravity (g/ml) | Moisture Content (%) | Ratio of particles smaller then 150 μm (%) | Easy Mixing | Surface Tension (mN/m) |
|---|---|---|---|---|---|---|---|---|---|---|
| | Name | Added Amount (ppm) | | | | | | | | |
| Example 1 | EXCEL 122V | 100 | 0.66 | 1.16 | 0.65 | 0.75 | 4.1 | 4.4 | YES | 54.8 |
| Example 2 | EXCEL 122V | 100 | 0.61 | — | — | — | 4.8 | 4.2 | YES | — |
| Com. Ex. 1 | — | — | 0.61 | 1.19 | 0.58 | 0.69 | 3.0 | 4.8 | YES | 69.5 |
| Com. Ex. 2 | — | — | 0.55 | — | — | — | 3.8 | 4.2 | YES | — |
| Com. Ex. 3 | — | — | 0.58 | — | — | — | 7.3 | 3.1 | NO | — |
| Com. Ex. 4 | EXCEL 122V | 100 | 0.60 | — | — | — | 6.7 | 3.4 | NO | — |
| Com. Ex. 5 | EXCEL 122V | 100 | 0.59 | — | — | — | 11.9 | 1.5 | NO | — |

Com. EX.: Comparative Example

TABLE 3

MOISTURE CONTENT AND DAMAGE RESISTANCE/BULK SPECIFIC GRAVITY WATER ABSORBING PROPERTIES

| | Surfactant whose HLB is 10 or less | | | | SFC | |
|---|---|---|---|---|---|---|
| | Name | Added Amount (ppm) | CRC (g/g) | FSR (g/g/s) | ($\times 10^{-7} \cdot$ cm$^3 \cdot$ sec$^{-1} \cdot$ g$^{-1}$) | D50 (μm) |
| Example 1 | EXCEL 122V | 100 | 25.7 | 0.37 | 134 | 383 |
| Com. Ex. 1 | — | — | 25.8 | 0.36 | 125 | 381 |

Com. Ex.: Comparative Example (Main Points)

It is shown from Tables 1 and 2 that the producing method of the present invention can provide the particulate water absorbing agent that has a high bulk specific gravity, has a low Hausner ratio, and is excellent in damage resistance. Moreover, it is shown from Table 3 that the producing method of the present invention does not impair an absorbing property of the particulate water absorbing agent.

From comparison of Example 1 with Comparative Examples 1 and 2, it is shown that, by adding the dispersion liquid containing the surfactant (i.e., specific surfactant) whose HLB is 10 or less, the bulk specific gravity is improved, the Hausner ratio is decreased, and the damage resistance is improved to an extent equivalent to the case where the substantially same amount of deionized water was added solely.

According to Comparative Examples 1 through 3, as the added amount of deionized water, which was added solely, increased from 0% to 5%, the moisture content increased from 3.0% to 7.3%, and the damage resistance was improved. Meanwhile, it is shown that the bulk specific gravity decreased from 0.61 to 0.58. In a case where the added amount of deionized water is excessively large, mixing property in the addition is significantly deteriorated. From this, it seems that the particulate water absorbing agent aggregated together and therefore the bulk specific gravity decreased.

From comparison of Examples 1 and 2 with Comparative Examples 4 and 5, it is shown that, as the amount of deionized water added simultaneously with the surfactant whose HLB is 10 or less increases, the damage resistance is improved but the mixing property is deteriorated and the bulk specific gravity is decreased. By setting the amount of deionized water, which is added simultaneously with the surfactant whose HLB is 10 or less, to an appropriate range, it is possible to improve the damage resistance and the bulk specific gravity without impairing the mixing property in the addition.

TABLE 4

INFLUENCE OF ADDITIVE TYPE & ADDING METHOD PREPARATION CONDITIONS

| | Additive | | | |
|---|---|---|---|---|
| | Name etc. | Adding Method (Timing) | Added Amount (ppm) | Added Amount of Water (%) |
| Example 3 | EXCEL F-40S | After SCL & adding LPIA | 100 | 0.99 |
| Example 4 | EXCEL S-95 | After SCL & adding LPIA | 100 | 0.99 |
| Example 5 | RHEODOL MS-80 | After SCL & adding LPIA | 100 | 0.99 |
| Example 6 | RHEODOL MO-60 | After SCL & adding LPIA | 100 | 0.99 |
| Example 7 | RHEODOL AO-15V | After SCL & adding LPIA | 100 | 0.99 |
| Example 8 | EMULGEN 306P | After SCL & adding LPIA | 100 | 0.99 |
| Example 9 | Glycerol monostearate | After SCL & adding LPIA | 100 | 0.99 |
| Example 10 | Glycerol monostearate/Glycerol distearate = 1/1 | After SCL & adding LPIA | 100 | 0.99 |
| Example 11 | EXCEL 122V | After SCL & adding LPIA | 80 | 0.70 |
| Example 12 | EXCEL 122V/RHEODOL TW-S120V = 1/1 | After SCL & adding LPIA | 75 | 1.49 |
| Example 13 | EXCEL 122V/RHEODOL TW-S120V = 1/1 | After SCL & adding LPIA | 100 | 1.98 |
| Example 14 | EXCEL 122V/RHEODOL TW-S120V = 9/1 | After SCL & adding LPIA | 75 | 0.82 |
| Example 15 | EXCEL 122V/RHEODOL TW-S120V = 1/9 | After SCL & adding LPIA | 30 | 2.97 |
| Example 16 | EXCEL 122V/EMANON CH-80 = 1/1 | After SCL & adding LPIA | 75 | 1.49 |
| Example 17 | EXCEL 122V/DEMOL N = 1/1 | After SCL & adding LPIA | 75 | 1.49 |
| Example 18 | EXCEL 122V/Sodium alginate = 1/1 | After SCL & adding LPIA | 75 | 1.49 |
| Example 19 | EXCEl 122V/POEM J-0021 = 1/1 | After SCL & adding LPIA | 75 | 1.49 |
| Example 20 | EXCEL 122V | After SCL | 100 | 0.99 |
| Example 21 | EXCEL 122V | After drying (pulverization, classification) | 100 | 0.99 |
| Example 22 | EXCEL S-95 | After SCL & adding LPIA (without heating after adding) | 100 | 0.99 |
| Example 23 | EXCEL 122V | In surface treatment | 100 | 2.60 |
| Example 24 | RHEODOL MS-80 | In surface treatment | 100 | 2.60 |
| Example 25 | EXCEL 122V/RHEODOL TW-S120V = 9/1 | In surface treatment | 100 | 2.60 |
| Example 26 | EXCEL 122V | After SCL & adding LPIA | 100 | 0.99 |
| Example 27 | EXCEL 122V | After SCL & adding LPIA | 100 | 0.99 |
| Com. Ex. 6 | RHEODOL TW-S120V | After SCL & adding LPIA | 100 | 0.99 |
| Com. Ex. 7 | EMANON CH-80 | After SCL & adding LPIA | 100 | 0.99 |
| Com. Ex. 8 | EXCEL 122V (ethyl alcohol solution) | After SCL & adding LPIA | 100 | 0.99 |
| Com. Ex. 9 | EXCEL 122V | After SCL & adding LPIA | 20 | 0.20 |
| Com. Ex. 10 | EXCEL 122V/RHEODOL TW-S120V = 1/9 | After SCL & adding LPIA | 10 | 0.99 |
| Com. Ex. 11 | EXCEL 122V | After SCL & adding LPIA | 10000 | 0 |
| Com. Ex. 12 | EXCEL 122V | After SCL, before adding LPIA | 100 | 0.99 |
| Com. Ex. 13 | EXCEL 122V | After SCL, mixed and added with LPIA | 100 | 0.99 |
| Com. Ex. 14 | EXCEL 122V | Added in SCL, then LPIA is added | 100 | 2.60 |
| Com. Ex. 15 | EXCEL 122V (mixed solution separated in 2 layers) | After SCL & adding LPIA | 100 | 0.99 |
| Com. Ex. 16 | StZn | After SCL | 6 | 0 |
| Com. Ex. 17 | PEG-400 | After SCL & adding LPIA | 500 | 0.28 |
| Com. Ex. 18 | After adding StZn (0.3%), add SOFTANOL 90 (0.1%) | After SCL | 3000 | 8.66 |

TABLE 4-continued

INFLUENCE OF ADDITIVE TYPE & ADDING METHOD PREPARATION CONDITIONS

| | Additive | | Added Amount (ppm) | Added Amount of Water (%) |
|---|---|---|---|---|
| | Name etc. | Adding Method (Timing) | | |
| Com. Ex. 19 | StZn(1%) & EMAL 20C (0.1%) are mixed and added | After SCL | 10000 | 5.86 |
| Com. Ex. 20 | — | — | — | 0 |

Com. Ex.: Comparative Example
SCL: Surface Crosslinking
LPIA: Liquid Permeability Improving Agent

TABLE 5

INFLUENCE OF ADDITIVE TYPE & ADDING METHOD
PHYSICAL PROPERTIES SUCH AS POWDER CHARACTERISTICS

| | Additive | | Bulk | | Loose Bulk | Tight Bulk | | |
|---|---|---|---|---|---|---|---|---|
| | Name etc. & Adding Method | Added Amount (ppm) | Specific Gravity (g/ml) | Hausner Ratio | Specific Gravity (g/ml) | Specific Gravity (g/ml) | Moisture Content (%) | Surface Tension (mN/m) |
| Example 3 | EXCEL P-40S | 100 | 0.68 | 1.14 | 0.66 | 0.76 | — | 67.3 |
| Example 4 | EXCEL S-95 | 100 | 0.66 | — | — | — | — | 65.3 |
| Example 5 | RHEODOL MS-60 | 100 | 0.66 | 1.16 | 0.67 | 0.78 | 4.0 | 65.8 |
| Example 6 | RHEODOL MO-60 | 100 | 0.65 | 1.17 | 0.65 | 0.76 | — | 59.7 |
| Example 7 | RHEODOL AO-15V | 100 | 0.62 | — | — | — | — | — |
| Example 8 | EMULGEN 306P | 100 | 0.61 | — | — | — | 4.4 | — |
| Example 9 | Glycerol monostearate | 100 | 0.68 | — | — | — | — | — |
| Example 10 | Glycerol monostearate/Glycerol distearate = 1/1 | 100 | 0.68 | — | — | — | — | — |
| Example 11 | EXCEL 122V | 80 | 0.67 | — | — | — | — | 60.7 |
| Example 12 | EXCEL 122V/RHEODOL TW-S120V = 1/1 | 75 | 0.68 | — | — | — | 4.5 | 54.2 |
| Example 13 | EXCEL 122V/RHEODOL TW-S120V = 1/1 | 100 | 0.66 | — | — | — | — | 51.6 |
| Example 14 | EXCEL 122V/RHEODOL TW-S120V = 9/1 | 75 | 0.66 | 1.15 | 0.66 | 0.76 | 3.8 | 65.1 |
| Example 15 | EXCEL 122V/RHEODOL TW-S120V = 1/9 | 30 | 0.66 | — | — | — | — | 50.9 |
| Example 16 | EXCEL 122V/EMANON CH-80 = 1/1 | 75 | 0.67 | — | — | — | 4.7 | 57.0 |
| Example 17 | EXCEL 122V/DEMOL N = 1/1 | 75 | 0.66 | — | — | — | 4.6 | 58.5 |
| Example 18 | EXCEL 122V/Sodium alginate = 1/1 | 75 | 0.66 | 1.17 | 0.64 | 0.75 | 4.5 | 60.5 |
| Example 19 | EXCEL 122V/POEM J-0021 = 1/1 | 75 | 0.66 | — | — | — | — | 58.2 |
| Example 20 | EXCEL 122V (without LPIA) | 100 | 0.67 | 1.16 | 0.65 | 0.75 | — | — |
| Example 21 | EXCEL 122V (without SCL, LPIA) | 100 | 0.62 | — | — | — | — | — |
| Example 22 | EXCEL S-95 (without heating after adding LPIA) | 100 | 0.56 | 1.14 | 0.67 | 0.76 | 4.3 | — |
| Example 23 | EXCEL 122V (added in ST. without LPIA) | 100 | 0.67 | — | — | — | 1.2 | — |
| Example 24 | RHEODOL MS-60 (added in ST. without LPIA) | 100 | 0.67 | — | — | — | 1.1 | — |
| Example 25 | EXCEL 122V/RHEODOL TW-S120V = 9/1 (added in ST. without LPIA) | 100 | 0.67 | — | — | — | 1.1 | — |
| Example 26 | EXCEL 122V (high crosslinking) | 100 | 0.68 | — | — | — | — | — |
| Example 27 | EXCEL 122V (low crosslinking) | 100 | 0.70 | — | — | — | — | — |
| Com. Ex. 6 | RHEODOL TW-S120V | 100 | 0.58 | 1.23 | 0.58 | 0.71 | — | — |
| Com. Ex. 7 | EMANON CH-80 | 100 | 0.60 | 1.18 | 0.52 | 0.73 | — | — |
| Com. Ex. 8 | EXCEL 122V (ethyl alcohol solution) | 100 | 0.59 | 1.19 | 0.58 | 0.69 | — | 58.7 |
| Com. Ex. 9 | EXCEL 122V | 20 | 0.59 | — | — | — | — | 61.8 |
| Com. Ex. 10 | EXCEL 122V/RHEODOL TW-S120V = 1/9 | 10 | 0.58 | — | — | — | — | 56.9 |
| Com. Ex. 11 | EXCEL 122V | 10000 | 0.59 | — | — | — | 3.0 | — |
| Com. Ex. 12 | EXCEL 122V (added before adding LPIA) | 100 | 0.59 | — | — | — | — | — |
| Com. Ex. 13 | EXCEL 122V (After SCL, added with LPIA) | 100 | 0.60 | — | — | — | — | — |
| Com. Ex. 14 | EXCEL 122V (added in SCL, then LPIA is added) | 100 | 0.59 | 1.18 | 0.63 | 0.74 | — | 72.6 |
| Com. Ex. 15 | EXCEL 122V (mixed solution separated in 2 layers) | 100 | 0.60 | — | — | — | — | — |
| Com. Ex. 16 | StZn | 6 | 0.70 | — | — | — | — | 73.0 |
| Com. Ex. 17 | PEG-400 | 500 | 0.69 | — | — | — | — | — |
| Com. Ex. 18 | After adding StZn(0.3%), and SOFTANOL 90(0.1%) | 3000 | Unmeasurable | — | — | — | — | — |
| Com. Ex. 19 | StZn(1%) & EMAL 20C(0.1%) are mixed and added | 10000 | 0.59 | — | — | — | — | — |
| Com. Ex. 20 | — | — | 0.63 | — | — | — | — | — |

Com. Ex.: Comparative Example
SCL: Surface Crosslinking
LPIA: Liquid Permeability Improving Agent
ST: surface Treatment

TABLE 6

INFLUENCE OF ADDITIVE TYPE & ADDING METHOD WATER ABSORBING PROPERTIES

| | Additive | | | | SFC | |
|---|---|---|---|---|---|---|
| | Name etc. & Adding Method | Added Amount (ppm) | CRC (g/g) | FSR (g/g/s) | ($\times 10^{-7} \cdot$ cm3 $\cdot$ sec $\cdot$ g$^{-1}$) | DSC (μm) |
| Example 3 | EXCEL P-40S | 100 | 27.6 | — | 87 | — |
| Example 4 | EXCEL S-95 | 100 | 26.8 | — | — | — |
| Example 5 | RHEODOL MS-60 | 100 | 26.2 | 0.36 | 128 | 362 |
| Example 6 | RHEODOL MO-60 | 100 | 25.8 | — | — | — |
| Example 7 | RHEODOL AO-15V | 100 | 26.5 | — | — | — |
| Example 11 | EXCEL 122V | 80 | 27.0 | 0.41 | — | 370 |
| Example 12 | EXCEL 122V/RHEODOL TW-S120V = 1/1 | 75 | 26.5 | 0.37 | 124 | — |
| Example 14 | EXCEL 122V/RHEODOL TW-S120V = 9/1 | 75 | 26.2 | 0.38 | 118 | 372 |
| Example 16 | EXCEL 122V/EMANON CH-80 = 1/1 | 75 | 26.1 | — | 131 | — |
| Example 17 | EXCEL 122V/DEMOL N = 1/1 | 75 | 26.1 | — | 122 | — |
| Example 18 | EXCEL 122V/Sodium alginate = 1/1 | 75 | 26.5 | — | 119 | 378 |
| Example 19 | EXCEL 122V/POEM J-0021 = 1/1 | 75 | 26.3 | — | 123 | — |
| Example 20 | EXCEL 122V (without LPIA) | 100 | 27.6 | — | — | — |
| Example 23 | EXCEL 122V (added in ST. without LPIA) | 100 | 28.1 | — | — | — |
| Example 24 | RHEODOL MS-60 (added in ST. without LPIA) | 100 | 28.1 | — | — | — |
| Example 25 | EXCEL 122V/RHEODOL TW-S120V = 9/1 (added in ST. without LPIA) | 100 | 26.0 | — | — | — |
| Example 26 | EXCEL 122V (high crosslinking) | 100 | 39.3 | 0.30 | — | 349 |
| Example 27 | EXCEL 122V (low crosslinking) | 100 | 27.3 | 0.38 | — | — |
| Com. Ex. 6 | RHEODOL TW-S120V | 100 | 26.8 | — | — | 372 |
| Com. Ex. 7 | EMANON CH-80 | 100 | 27.7 | — | — | — |
| Com. Ex. 8 | EXCEL 122V (ethyl alcohol solution) | 100 | 27.6 | 0.41 | 91 | 367 |
| Com. Ex. 9 | EXCEL 122V | 20 | 27.1 | 0.42 | — | 378 |
| Com. Ex. 12 | EXCEL 122V (added before adding LPIA) | 100 | 26.7 | 0.40 | 113 | — |
| Com. Ex. 13 | EXCEL 122V (After SCL, added with LPIA) | 100 | 26.6 | 0.41 | 114 | 379 |
| Com. Ex. 14 | EXCEL 122V (added in SCL, then LPIA is added) | 100 | 31.3 | — | — | — |
| Com. Ex. 16 | StZn | 6 | 30.0 | 0.17 | 42 | — |
| Com. Ex. 17 | PEG-400 | 500 | 27.2 | 0.20 | 68 (GBP) | — |
| Com. Ex. 18 | After adding StZn(0.3%), and SOFTANOL 90(0.1%) | 3000 | 25.9 | — | — | — |
| Com. Ex. 19 | StZn(1%) & EMAL 20C(0.1%) are mixed and added | 10000 | 25.6 | — | — | — |
| Com. Ex. 20 | — | — | 27.5 | 0.38 | — | — |

Com. Ex.: Comparative Example
SCL: Surface Crosslinking
LPIA: Liquid Permeability Improving Agent
ST: surface Treatment (Main Points)

It is shown from Tables 4 through 6 that the producing method of the present invention can provide the particulate water absorbing agent whose water absorbing speed is improved and which has the high bulk specific gravity, i.e., 0.61 or higher and the low Hausner ratio, i.e., less than 1.18.

From comparison of Examples 3 through 10 with Comparative Examples 6 and 7, it is shown that the bulk specific gravity is improved to 0.61 or higher and the Hausner ratio is decreased to less than 1.18 by adding the surfactant whose HLB is 10 or less. Moreover, it is also shown that, among the surfactants whose HLB is 10 or less, particularly glycerine fatty acid ester brings about an excellent effect.

It is shown from Examples 9 and 10 that glycerol stearate improves the bulk specific gravity as with the case where monoester is used alone, even in a case where glycerol stearate contains both monoester and diester.

It is shown from Examples 12 through 19 that, when the dispersion liquid containing the surfactant whose HLB is 10 or less is prepared, a nonionic surfactant whose HLB is greater than 10, an ionic surfactant, and a water-soluble polymer can be used together as dispersing agents.

From comparison of Example 1 with Comparative Examples 8 and 15, it is shown that a uniform solution or phase-separated solution of the surfactant whose HLB is 10 or less cannot bring about the effect, and only in a case where the surfactant whose HLB is 10 or less is added as a dispersion liquid to the water absorbent resin particles, the effects of improving bulk specific gravity (and decreasing Hausner ratio) can be brought about.

From comparison of Examples 1, 11 through 13, and 15 with Comparative Examples 9 through 11, it is shown that (i) there is an optimal added amount (i.e., 30 ppm to 150 ppm relative to water absorbent resin) of the surfactant whose HLB is 10 or less, (ii) in a case where the added amount is excessively small, the effect of improving bulk specific gravity cannot be brought about, and (iii) in a case where the added amount is excessively large, the bulk specific gravity tends to decrease and further the surface tension decreases.

From Examples 20 and 21, it is shown that the bulk specific gravity is improved (and Hausner ratio is decreased) by adding the surfactant whose HLB is 10 or less, even in a case where no liquid permeability improving agent (water-soluble polyvalent metal salt) is added to the water absorbent resin particles.

From Examples 4 and 22, it is shown that the heating after adding the surfactant whose HLB is 10 or less does not influence the effect of improving the bulk specific gravity (and decreasing the Hausner ratio).

From comparison of Example 1 with Comparative Examples 12 through 14, it is shown that, in a case where the liquid permeability improving agent is added, the surfactant whose HLB is 10 or less needs to be added after the liquid permeability improving agent is added.

From Examples 1 and 23 through 25, it is shown that the effect of improving bulk specific gravity can be brought about even by adding the surfactant whose HLB is 10 or less as a mixture with the surface crosslinking agent which is heated at high temperature. In this case, however, the moisture content is greatly decreased.

From comparison of Example 1 with Comparative Examples 16 and 17, it is shown that the prior arts (Patent Literatures 37 and 38) are high in bulk specific gravity but are low in FSR.

From comparison of Example 1 with Comparative Examples 18 and 19, it is shown that zinc stearate and the surfactant, which are added in the prior arts (Patent Literatures 39 and 40), cannot bring about the effect of improving bulk specific gravity.

From comparison of Examples 1, 26, and 27 with Comparative Examples 1 and 20, it is shown that, even in a case where the method of preparing water absorbent resin particles is different or even in a case where the CRC (water absorption capacity without load) is different, the effect of improving bulk specific gravity is not influenced by the preparation method or the CRC.

(Main Points of Present Invention)

The method of the present invention for producing a water absorbing agent includes: a surfactant adding step of adding a surfactant whose HLB is 10 or less, the surfactant adding step being the step of adding a dispersion liquid, which contains the surfactant equivalent to 30 parts by weight to 150 parts by weight (30 mass ppm to 150 mass ppm relative to water absorbent resin), relative to 1000000 parts by weight of a water absorbent resin solid content, and the surfactant adding step being carried out after a drying step, and in a case where a water-soluble polyvalent metal salt adding step is carried out after the drying step, the surfactant adding step being carried out after the water-soluble polyvalent metal salt adding step.

In the producing method, it is more preferable that, in a case where a surface crosslinking agent adding step is carried out after the drying step, the surfactant adding step is carried out similarly with the surface crosslinking agent adding step or after the surface crosslinking agent adding step.

Moreover, in the producing method, it is more preferable that the surfactant is at least one compound selected from polyoxyethylene alkyl ether, sorbitan fatty acid ester, polyoxyethylene sorbitan fatty acid ester, glycerine fatty acid ester, and sucrose fatty acid ester. Further, in the present invention, it is more preferable that the surfactant is glycerine fatty acid ester.

Moreover, in the producing method, it is more preferable that, in the surfactant adding step, the dispersion liquid of the surfactant is added which contains 0.5 part by weight or more and 3.0 parts by weight or less of water relative to 100 parts by weight of the water absorbent resin.

Moreover, in the producing method, it is more preferable that the dispersion liquid of the surfactant is obtained by (i) stirring at a rotating speed of 1000 rpm or higher or at a blade tip peripheral velocity (of stirring member/impeller) of 2.5 m/s or higher for 1 minute or longer at 40° C. or higher and/or (ii) using a water-soluble dispersing agent. Further, in the producing method, it is more preferable that the water-soluble dispersing agent is a nonionic surfactant whose HLB is greater than 10, an ionic surfactant, or a water-soluble polymer.

Moreover, according to the producing method, when a drying step (drying step after addition) for causing a moisture content to be 6 wt % or less is carried out after the surfactant adding step, it is possible to sufficiently bring about the effect of the present invention. Note that the drying step after addition is not limited to an intentional heating operation or an intentional blowing operation and encompasses a drying operation including reduction in moisture content by natural evaporation.

Further, the producing method is suitable for a method for producing the water absorbing agent in which method a water absorbing speed (FSR) of the water absorbing agent is 0.25 [g/g/s] or more.

The water absorbing agent of the present invention including a polyacrylic acid (salt)-based water absorbent resin as a main component, the water absorbing agent having a Hausner ratio of less than 1.18 and a water absorbing speed (FSR) of 0.25 [g/g/s] or more.

The water absorbing agent of the present invention is a water absorbing agent including a polyacrylic acid (salt)-based water absorbent resin as a main component, the water absorbing agent having a moisture content of 3.0 mass % to 6.0 mass % or further including a liquid permeability improving agent, and the water absorbing agent further including 30 parts by weight to 150 parts by weight (30 mass ppm to 150 mass ppm relative to water absorbent resin) of a surfactant, whose HLB is 10 or less, relative to 1000000 parts by weight of a water absorbent resin solid content.

The water absorbing agent is an excellent water absorbing agent having a bulk specific gravity of 0.61 g/ml to 0.80 g/ml. The water absorbing agent more preferably further includes a liquid permeability improving agent. Moreover, the water absorbing agent has an excellent property, that is, a ratio of particles smaller than 150 μm after an impact resistance test is 0 mass % to 4.6 mass %.

INDUSTRIAL APPLICABILITY

The water absorbing agent and the method of producing the water absorbing agent of the present invention are mainly suitable for use in disposable articles, i.e., for absorbing articles such as a disposable diaper and a sanitary napkin and for an agriculture/horticulture water retention agent, an industrial waterproofing material, and the like.

The invention claimed is:

1. A water absorbing agent comprising a polyacrylic acid (salt)-based water absorbent resin as a main component,
said water absorbing agent having a Hausner ratio of less than 1.18, a water absorbing speed (FSR) of 0.25 [g/g/s] or more, and a bulk specific gravity of 0.61 g/ml or more and 0.80 g/ml or less.

2. The water absorbing agent as set forth in claim 1, further comprising a liquid permeability improving agent.

3. The water absorbing agent as set forth claim 1, wherein the amount of particles smaller than 150 μm after an impact resistance test is 0 mass % to 4.6 mass %.

4. The water absorbing agent of claim 1, wherein said water absorbing agent contains a surfactant having an HLB of 1 or more and 6 or less.

* * * * *